(12) United States Patent
Atwood

(10) Patent No.: US 11,253,549 B2
(45) Date of Patent: Feb. 22, 2022

(54) METHODS TO REBALANCE THE HYPOTHALAMIC-PITUITARY-GONADAL AXIS

(71) Applicant: JangoBio, LLC, Madison, WI (US)

(72) Inventor: Craig S. Atwood, Madison, WI (US)

(73) Assignee: JangoBio, LLC, Madison, WI (US)

( * ) Notice: Subject to any disclaimer, the term of this patent is extended or adjusted under 35 U.S.C. 154(b) by 0 days.

(21) Appl. No.: 14/718,390

(22) Filed: May 21, 2015

(65) Prior Publication Data

US 2015/0359822 A1    Dec. 17, 2015

Related U.S. Application Data

(60) Provisional application No. 62/002,305, filed on May 23, 2014.

(51) Int. Cl.
*A61K 35/28*    (2015.01)
*A61K 35/36*    (2015.01)
*A61K 31/568*   (2006.01)
*A61K 31/57*    (2006.01)
*A61K 31/566*   (2006.01)
*A61K 35/545*   (2015.01)
*A61K 35/55*    (2015.01)
*A61K 35/54*    (2015.01)
*A61K 35/15*    (2015.01)
*A61K 35/52*    (2015.01)

(52) U.S. Cl.
CPC ............ *A61K 35/28* (2013.01); *A61K 31/566* (2013.01); *A61K 31/568* (2013.01); *A61K 31/57* (2013.01); *A61K 35/15* (2013.01); *A61K 35/36* (2013.01); *A61K 35/52* (2013.01); *A61K 35/54* (2013.01); *A61K 35/545* (2013.01); *A61K 35/55* (2013.01)

(58) Field of Classification Search
CPC ........ A61K 35/28; A61K 35/51; A61K 35/36; A61K 31/568; A61K 38/1709; A61K 31/57; A61K 31/56
See application file for complete search history.

(56) References Cited

U.S. PATENT DOCUMENTS

| | | | |
|---|---|---|---|
| 6,503,894 B1 * | 1/2003 | Dudley | A61P 5/26 514/178 |
| 7,361,505 B1 | 4/2008 | Weiss et al. | |
| 7,368,115 B2 | 5/2008 | Ohta et al. | |
| 7,595,056 B1 * | 9/2009 | Mendis-Handagama | A61K 38/24 424/198.1 |
| 7,674,457 B2 | 3/2010 | Borlongan et al. | |
| 7,700,352 B2 | 4/2010 | Niwa et al. | |
| 7,846,898 B2 | 12/2010 | Weiss et al. | |
| 8,137,662 B2 | 3/2012 | Freeman et al. | |
| 8,143,220 B2 | 3/2012 | Weiss et al. | |
| 8,217,002 B2 | 7/2012 | Weiss et al. | |
| 8,435,949 B2 | 5/2013 | Weiss et al. | |
| 8,603,809 B2 | 12/2013 | Kruse | |
| 8,658,128 B2 | 2/2014 | Altschul et al. | |
| 2002/0168350 A1 | 11/2002 | Brazelton et al. | |
| 2003/0027804 A1 * | 2/2003 | van der Hoop | A61P 43/00 514/177 |
| 2003/0100997 A1 | 5/2003 | Dunnington et al. | |
| 2004/0115175 A1 | 6/2004 | Blau et al. | |
| 2006/0234918 A1 | 10/2006 | Gregory et al. | |
| 2007/0026520 A1 | 2/2007 | Kelly | |
| 2007/0128174 A1 | 6/2007 | Kleinsek et al. | |
| 2007/0166289 A1 | 7/2007 | Hathaway et al. | |
| 2007/0179092 A1 | 8/2007 | Ohta et al. | |
| 2008/0280360 A1 | 11/2008 | Kaplan et al. | |
| 2009/0099623 A1 | 4/2009 | Bentwich | |
| 2009/0105521 A1 | 4/2009 | Bentwich | |
| 2009/0197796 A1 | 8/2009 | Gregory et al. | |
| 2009/0274668 A1 | 11/2009 | Thompson et al. | |
| 2010/0028361 A1 | 2/2010 | Smith et al. | |
| 2010/0034779 A1 | 2/2010 | Guan et al. | |
| 2010/0062477 A1 | 3/2010 | Yu | |
| 2010/0135980 A1 | 6/2010 | Rodriguez | |
| 2010/0173344 A1 | 7/2010 | Yu | |
| 2010/0310532 A1 | 12/2010 | Hare et al. | |
| 2011/0081323 A1 | 4/2011 | Kleinsek et al. | |
| 2011/0104100 A1 | 5/2011 | Riordan et al. | |
| 2011/0286998 A1 | 11/2011 | Gregory et al. | |
| 2011/0293685 A1 | 12/2011 | Kuo et al. | |
| 2011/0312091 A1 | 12/2011 | Zhao et al. | |
| 2012/0070445 A1 | 3/2012 | Smith et al. | |
| 2012/0276070 A1 | 11/2012 | Musick | |
| 2012/0322856 A1 | 12/2012 | Dimmeler et al. | |
| 2013/0243739 A1 | 9/2013 | Burt | |
| 2015/0359822 A1 | 12/2015 | Atwood | |
| 2018/0221419 A1 | 8/2018 | Atwood et al. | |

FOREIGN PATENT DOCUMENTS

| | | | |
|---|---|---|---|
| WO | 2013065763 A1 | 5/2013 | |
| WO | 2017048193 A1 | 3/2017 | |

OTHER PUBLICATIONS

Sun et al. Leydig cell transplantation restores androgen production in surgically castrated prepubertal rats. Asian Journal of Andrology (2009), v11, p. 405-109.*
Durruthy et al. Fate of induced pluripotent stem cells following transplantation to murine seminiferous tubules. Human Molecular Genetics (epub. Jan. 2014), v23(12), p. 3071-3084.*
Manzoor et al. Serum Inhibin B as a Diagnostic Marker of Male Infertility. J Ayub Med Coll Abbottabad (2012), v24(3-4), p. 113-116.*
Chatterjee et al. Patterns of Leydig cell insufficiency in adult males following bone marrow transplantation for haematological malignancies. Bone Marrow Transplant (2001), v28(5), p. 497-502.*
Shores et al. Testosterone Treatment and Mortality in Men with Low Testosterone Levels. J Clin Endocrinol Metab (2012), V97(6), p. 2050-2058.*

(Continued)

*Primary Examiner* — Sean C. Barron
(74) *Attorney, Agent, or Firm* — BakerHostetler

(57) ABSTRACT

A hypothalamic-pituitary-gonadal (HPG) axis of a patient in need thereof is rebalanced by administering a therapeutically effective amount of at least one donor cell.

20 Claims, 2 Drawing Sheets

(56) References Cited

OTHER PUBLICATIONS

Passweg et al. Hematopoietic stem cell transplantation: a review and recommendations for follow-up care for the general practitioner. Swiss Med Wkly (2012), 142, w13696, 15 pages. (Year: 2012).*
Wei et al. Mesenchymal stem cells: a new trend for cell therapy. Acta Pharmacol Sin (2013); 34(6), 747-754. (Year: 2013).*
Lim et al. Hematopoietic cell differentiation from embryonic and induced pluripotent stem cells. Stem Cell Res Ther (2013) 4(3), 11 pages. (Year: 2013).*
Xu et al. Concise Review: Chemical Approaches for Modulating Lineage-Specific Stem Cells and Progenitors. Stem Cells Translational Medicine (2013), 2, 355-361. (Year: 2013).*
Pournasr et al. Concise Review: Alchemy of Biology: Generating Desired Cell Types from Abundant and Accessible Cells. Stem Cells (2011), 29, 1933-1941. (Year: 2011).*
Guiterrez-Aranda et al. Human Induced Pluripotent Stem Cells Develop Teratoma More Efficiently and Faster Than Human Embryonic Stem Cells Regardless the Site of Injection. Stem Cells (2010), 28(9), p. 1568-1570. (Year: 2010).*
Blum et al. The tumorigenicity of human embryonic stem cells . . . Adv. Cancer Res. (2008), 100, 133-158, Abstract only. (Year: 2008).*
Fu et al. Regenerative medicine: Transdifferentiation in vivo. Cell Research (2013), 24, 141-142. (Year: 2014).*
M.K. Brawer. Testosterone Replacement in Men With Andropause: An Overview. Rev. Urol. (2004), 6(Suppl. 6), S9-S15. (Year: 2004).*
Yazawa et al. Differentiation of mesenchymal stem cells into gonad and adrenal steroidogenic cells. World Journal of Stem Cells (Apr. 2014), 6(2), 203-212. (Year: 2014).*
Del Tredici et al. Identification of the First Synthetic Steroidogenic Factor 1 Inverse Agonists: Pharmacological Modulation of Steroidogenic Enzymes. Molecular Pharmacology (2008), 73(6), 900-908. (Year: 2008) [Cited in related U.S. Appl. No. 15/947,304].
Whitby et al. (Journal of Medicinal Chemistry (2011), 54, 2266-2281. Small Molecule Agonists of the Orphan Nuclear Receptors Steroidogenic Factor-1 (SF-1, N R5A 1) and Liver Receptor Homologue-1 (LRH-1, N R5A2). (Year: 2011) [Cited in related U.S. Appl. No. 15/947,304].
Chen et al. Stem Leydig Cells: From Fetal to Aged Animals. Birth Defects Res C Embryo Today (2010), 90(4), 21 page reprint. (Year: 2010) [Cited in related U.S. Appl. No. 15/947,304].
Hummitzsch et al. Stem Cells, Progenitor Cells, and Lineage Decisions in the Ovary. Endocrine Reviews (2015), 36(1), 65-91 (Year: 2015) [Cited in related U.S. Appl. No. 15/947,304].
Hormone (The Macmillan Encyclopedia (2003), 1 page. (Year: 2003) [Cited in related U.S. Appl. No. 15/947,304].
Tosh et al. Conversion of pancreatic cells to hepatocytes. 2002, Biochem Soc Trans 30: 51-55. (Year: 2002) [Cited in related U.S. Appl. No. 15/947,304].
Castro et al. Failure of Bone Marrow Cells to Transdifferentiate into Neural Cells in Vivo. 2002, Science 297: 1299 (Year: 2002) [Cited in related U.S. Appl. No. 15/947,304].
Mezey et al. and Castro et al. (Science (2003), 299, 1184b-c. (Year: 2003) [Cited in related U.S. Appl. No. 15/947,304].
Reinecke et al. Skeletal Muscle Stem Cells Do Not Transdiferentiate Into Cardiomyocytes After Cardiac Grafting. 2002, J Mol Cell Cardiol 34: 241-249. (Year: 2002) [Cited in related U.S. Appl. No. 15/947,304].
Murry et al. Haematopoietic stem cells do not transdifferentiate into cardiac myocytes in myocardial Infarcts. 2004, Nature 428: 664-668 (Year: 2004) [Cited in related U.S. Appl. No. 15/947,304].
Hynes K., Menicanin D., Gronthos S., Bartold M.P. (2014) Differentiation of iPSC to Mesenchymal Stem-Like Cells and Their Characterization. In: Turksen K., Nagy A. (eds) Induced Pluripotent Stem (iPS) Cells. Methods in Molecular Biology, vol. 1357. Humana Press, New York, NY (Year: 2014) [Cited in related U.S. Appl. No. 15/947,304].
S. S. Negus. Some implications of receptor theory for in vivo assessment of agonists, antagonists and inverse agonists. Biochemical Pharmacology (2006), 71, 1663-1670. (Year: 2006) [Cited in related U.S. Appl. No. 15/947,304].
Chen et al., "Wt1 Directs the Lineage Specification of Sertoli and Granulosa Cells by Repressing Sf1 Expression," The Company of Biologists, Development, 2017, vol. 144, No. 1, pp. 44-53.
Atwood et al. "Does the Degree of Endocrine Dyscrasia Post-Reproduction Dictate Post-Reproductive Lifespan Lessons from *Semelparous* and *Iteroparous* Species" GeroScience, 2017, vol. 39, pp. 103-116.
Veiga-Lopez et al. "Developmental Programming: Prenatal Testosterone Excess Disrupts Anti-Mullerian Hormone Expression in Preantral and Antral follicles," Fertility and Sterility, Mar. 2012, vol. 97, No. 3, pp. 748-756.
Yonker et al. "Hypothalamic-Pituitary-Gonadal Axis Homeostasis Predicts Longevity," Age, 2013, vol. 35, No. 1, pp. 129-138.
Zang et al. "Transplantation of CD51+ Stem Leydig Cells: A New Strategy for the Treatment of Testosterone Deficiency," Stem Cells, 2017, vol. 35, No. 5, pp. 1222-1232.
International Search Report and Written Opinion issued in PCT/US2019/026305, dated Jul. 11, 2019.

* cited by examiner

METHODS TO REBALANCE THE HYPOTHALAMIC-PITUITARY-GONADAL AXIS

CROSS-REFERENCE TO RELATED APPLICATION

This application is a non-provisional application and claims priority to U.S. Provisional Application Ser. No. 62/002,305, filed on May 23, 2014, titled, "METHODS TO REBALANCE THE HYPOTHALAMIC-PITUITARY-GONADAL AXIS: APPLICATIONS IN DELAYING AGE-RELATED DISEASES AND EXTENSION OF LONGEVITY", the disclosure of which is incorporated herein by reference in its entirety.

FIELD OF THE INVENTION

The present disclosure relates to hormone replacement. More particularly, the disclosure relates to a method of maintaining in balance or rebalancing, the hypothalamic-pituitary-gonadal (HPG) axis.

BACKGROUND OF THE INVENTION

Aging is regulated by reproductive hormones that act to promote growth and development early in life in order to achieve reproduction, maintain tissue function during reproductive life but later in life become dysregulated and drive senescence via altered cell cycle signaling (Bowen and Atwood 2004).

The principal hormones responsible for regulating reproductive function include the centrally and peripherally (primarily the gonads) produced hormones. In the human and many mammals the centrally produced hormones include gonadotropin releasing hormone (GnRH) from the hypothalamus and the gonadotropins, luteinizing hormone (LH) and follicle stimulating hormone (FSH), from the pituitary. Peripherally produced hormones include estrogens, progestagens, androgens and inhibins that are primarily of gonadal origin while activins, follistatin and myostatin are produced in all tissues including the gonads (Can 1998). The levels of each of these hormones are regulated by a complex feedback loop—GnRH secretion from the hypothalamus stimulates the anterior pituitary to secrete the gonadotropins, LH and FSH, which then bind to receptors in the gonads and stimulate oogenesis/spermatogenesis as well as sex steroid and inhibin production (reviewed in Reichlin (Reichlin 1998)). The sex steroids then feedback to the hypothalamus and pituitary, resulting in a decrease in gonadotropin secretion (reviewed in (Thorner, et al. 1998)). Activins, which are produced in many tissues, also stimulate gonadotropin secretion (Ling, et al. 1986; Vale, et al. 1986). Activins' stimulation of gonadotropin production is inhibited by inhibins and follistatin and likely myostatin, all of which are able to irreversibly bind to activins and prevent them from binding to their receptors (Cash, et al. 2012; DeKretser, et al. 2002; Gray, et al. 2002). Since inhibins are primarily produced in the gonads and their production is dependent on folliculogenesis/spermatogenesis (Knight and Glister 2001), they are intimately involved in the regulation of the HPG axis and are in fact a direct indicator of fertility.

The HPG axis is primarily regulated via the above mechanism. However, multiple other axes involving the hormones of the HPG axis have been found to exist throughout the body. Taking the brain as an example, these 'mini-HPG' axes include the *Gonadal-Brain Neurosteroid Feedback Axis*, the *Pituitary-Brain Neurosteroid Feedback Axis*, the *Brain Neurosteroid Feedback Axis* and the *HPG-Extra-Hypothalamic Brain Neurosteroid Axis* (see FIG. 5 in (Meethal, et al. 2009b)). In essence, the brain contains all the hormones, receptors, and cholesterol transport machinery of the HPG axis, and is regulated via feedback mechanisms. This mechanism may be of crucial importance following menopause and during andropause to compensate for the loss of circulating sex steroids (Meethal et al. 2009). This is supported by the findings that brain steroid levels are decreased in men and women with Alzheimer's disease (AD) compared with controls (Rosario, et al. 2011; Rosario, et al. 2004; Yue, et al. 2005). Similar interconnected feedback loops are expected for the hypothalamic-pituitary-adrenal axis, and other endocrine axes, and for the regulation of sex hormones in all other sex hormone producing tissues of the body including the placenta.

Gonadal produced sex hormones therefore regulate HPG hormones in all tissues of the body. Likewise, hypothalamic and pituitary produced hormones can also influence the production of sex hormones in all tissues of the body.

Hormones produced by the gonads (gonadal hormones) include but are not limited to: sex steroids and their conjugated forms (17β-estradiol, 2-methoxyestradiol, estrone, estriol, pregnenolone, 17α-hydroxypregnenolone, 17α-hydroxyprogesterone, progesterone, testosterone, dihydrotestosterone, androstenedione, 1-andro stenediol, 4-androstenediol, 5-androstenediol, dehydroepiandrosterone, dihydroprogesterone, allopregnanlone, 17α-dihydroxyprogesterone, 17α-hydroxy allopregnanlone, 5α-androstenedione, androsterone, 5-androstenediol, 3α-androstenediol, 3β-androstenediol, α-triols, glucuronides, etiocholanolone, etiocholandione, etiocholandiol, 11-oxo-etiocholanolone, 11β-hydroxyandrosterone, 11β-hydroxy etiocholanolone, 16α-hydroxy dehydroepiandrosterone, 5-androstene-3β, 16α,17β triol, 5-pregnene-3β,16α,17β triol, pregnanetriol, 11-oxo-pregnanetriol, pregnandione, pregnantrione, 17α-hydroxypregnanolone, pregnandiol, pregnandiol-20β), inhibins, activins, anti-Müllerian hormone, steroidogenic factor-1, liver receptor homolog-linsulin-like growth factor, insulin, fibroblast growth factors, stem cell factor, transforming growth factor-β, bone morphogenetic proteins (BMP), BMP4, growth differentiation factors (GDF9, GDF11).

Reproductive hormones are required for the normal maintenance of all bodily tissues and their functions (Atwood and Bowen 2011). Receptors for reproductive tissues are found on almost every cell type in the human body (Atwood and Vadakkadath Meethal 2011a, b; Atwood, et al. 2005; Gallego, et al. 2010; Gallego, et al. 2009; Meethal, et al. 2009a; Meethal, et al. 2005; Vadakkadath Meethal and Atwood 2005; Wilson, et al. 2006). Reproductive hormones signal via these receptors to drive cell division (e.g. luteinizing hormone, follicle-stimulating hormone, gonadotropin-releasing hormone) while certain other reproductive hormones promote cell differentiation (i.e. cell specification and function, e.g. sex steroids, activins, inhibins, follistatin, myostatin). When these hormones are in balance there is appropriate cell division and differentiation for the replacement of cells lost during normal tissue maintenance. This turnover of cells in tissues allows normal tissue function.

The dysregulation of the reproductive axis (hypothalamic-pituitary-gonadal axis; HPG; FIG. 1A and FIG. 1B), otherwise known as reproductive endocrine dyscrasia, leads to altered (dyotic) signaling to all cells in the body. Since the hormones of the reproductive HPG axis are involved in cellular mitogenesis and differentiation, this dyotic signaling leads to aberrant cell cycle signaling, cellular dysregulation and dysfunction, and/or cell death in all tissues of the body, eventually leading to organ failure and death (Atwood and Bowen 2011; Bowen and Atwood 2004).

Reproductive endocrine dyscrasia that leads to dysregulation of the mini-HPG axes present in tissues throughout the body leads to dyotic signaling, aberrant cell cycle signaling, cellular dysregulation and dysfunction, and/or cell death in those tissues of the body, eventually leading to organ failure and death.

The age-related dysregulation of the HPG axis in women (FIG. 1A) is a direct result of the loss of ovarian follicles in the female (Bowen and Atwood 2004); primordial follicle numbers fall from ~1,000,000 at birth to a few thousand non-functional follicles at menopause (Wallace and Kelsey 2010). Granulosa and thecal cells of the follicle produce sex hormones (e.g. estrogens, progestagens, inhibins) that promote the release of the ovum (ovulation), but these hormones also negatively feedback on the HP to maintain the axis in equilibrium. With the loss of follicles, gonadal sex hormones are no longer synthesized and this results in the loss of negative feedback on the hypothalamus and pituitary, leading to the dysregulation of the HPG axis, and menopause. The timing of menopause is variable (average age is approximately 51 in the USA) due to the variance in the total number of follicles that a female is born with together with the rate at which follicles are lost throughout the female reproductive period. Endocrine dyscrasia also occurs following surgical removal of the ovaries and in certain disease states and conditions.

The age-related dysregulation of the HPG axis in men (FIG. 1B), which is more gradual and starts at around 30 years of age in men (FIG. 1B) is a direct result of the loss of testicular Leydig, Sertoli and other gonadal cells (Belanger, et al. 1994). Leydig and Sertoli cells are the male equivalent of granulosa and thecal cells; they are the testicular support cells that produce androgens, inhibins, anti-Müllerian hormone, estradiol, glial cell line-derived neurotrophic factor and other hormones required for spermatogenesis. Each year after the age of 30, there is a ~1-2% decrease in testosterone production by the testes that corresponds to a ~1-2% decrease in Leydig cell number (Belanger et al. 1994; Tserotas and Merino 1998). Endocrine dyscrasia also occurs following surgical removal of the testes and in certain disease states and conditions.

After menopause, and during andropause, the decrease in the production of gonadal inhibins (Reichlin 1998) leads to an increase in bioavailable activins (Gray, et al. 2002), thereby increasing hypothalamic GnRH and pituitary gonadotropins (MacConell, et al. 1999; Schwall, et al. 1988; Weiss, et al. 1993). Likewise, the concurrent decrease in gonadal sex steroid production results in a loss of hypothalamic feedback inhibition and also stimulates GnRH and gonadotropin production (Carr 1998). In women the loss of this negative feedback by estrogen and inhibins (Couzinet and Schaison 1993) results in a three- to four-fold and a four- to eighteen-fold increase in the concentrations of serum LH and FSH, respectively (Chakravarti, et al. 1976). Likewise, men also experience a greater than two-fold, and three-fold, increase in LH and FSH, respectively as their reproductive function deteriorates (Neaves, et al. 1984).

This reproductive endocrine dyscrasia, associated with menopause, andropause and hypogonadism, is associated with the development of numerous symptoms, and senescent and age-related diseases and conditions. The HPG axis also is dysregulated in a number of primary congenital, primary acquired, secondary congenital and secondary acquired conditions and diseases.

Maintaining the HPG axis in balance decreases the risk of developing senescent and age-related disease and extends longevity in humans. For example, menopause at a later age reduces the risk of morbidity and mortality; the incidence of cardiovascular disease, calcifications in the aorta, atherosclerosis, cognitive decline, bone fractures and certain cancers is reduced (see: (Atwood and Bowen 2011; Ossewaarde, et al. 2005; Yonker, et al. 2011); FIG. 2). Conversely, early reproductive endocrine dyscrasia occurring naturally or induced by bilateral oophorectomy in premenopausal women, increases risk of morbidity and mortality (Rocca, et al. 2006); the incidence of dementia, cognitive decline, stroke, fatal and non-fatal coronary heart disease, Parkinsonism, osteoporosis, hip fracture, lung cancer, depression and anxiety are increased (e.g. (Gleason, et al. 2005; Parker and Manson 2009; Rocca et al. 2006; Rocca, et al. 2008; Rocca, et al. 2012).

Manipulation of the HPG axis in model organisms provides strong evidence for a direct link between HPG axis balance and longevity (Arantes-Oliveira, et al. 2002). In Mammalia (*Mus musculus*), re-establishment of the negative feedback loops in the HPG axis of post-reproductive mice (11 months of age) following transplantation of reproductively viable ovaries from young mice (3 months of age) has been demonstrated to extend lifespan by up to 40% (Cargill, et al. 2003; Mason, et al. 2009). In Actinopterygii, certain long-lived species (including *Sebastes aleutianus* (Rougheye rockfish; >140 years) and *Sebastes alutus* (Pacific ocean perch; 98 years)) maintain their HPG axis in balance by maintaining a constant number of ovarian follicles (de Bruin, et al. 2004). In Insecta (*Drosophila melanogaster*) heterozygous for inactivating mutations in the ligand binding domain or DNA binding domain of ecdysone receptor there is a robust (typically 20-50%) lifespan-extension (Simon, et al. 2003). In Secernentea (*Caenorhabditis elegans*), suppression of GnRH receptor signaling significantly decreases reproduction 46% and prolongs lifespan 15% (23% at lower temperature) compared with wild-type worms (Vadakkadath Meethal, et al. 2006; Vadakkadath Meethal, Bowen and Atwood, unpublished data).

Strategies to completely rebalance the HPG axis have not been attempted. Supplemental add-back of one or more steroid hormones or drugs provides partial rebalancing of the HPG axis with decreases in menopausal and andropausal symptoms, and reduces the risk of morbidity and decreases mortality (reviewed in (Paganini-Hill, et al. 2006)). However, rebalancing this axis using one or two hormones or drugs is insufficient to completely rebalance the entire axis (Atwood and Bowen, 2011), and comes with the increased risk of neoplasia.

Accordingly, there is a need for balancing and maintaining in balance the HPG axis to address the problems described above and/or problems posed by other conventional approaches.

SUMMARY OF THE INVENTION

Embodiments of the present disclosure are capable of balancing and maintaining in balance the HPG axis, at least to some extent.

An embodiment of the invention pertains to a method of treating a patient. In this method, a hypothalamic-pituitarygonadal (HPG) axis of the patient in need thereof is rebalanced by administering a therapeutically effective amount of at least one donor cell.

Another embodiment of the invention relates to a method of reducing endocrine dyscrasia (dyosis) in a patient. In this method, a hypothalamic-pituitary-gonadal (HPG) axis of the patient in need thereof is rebalanced by administering a therapeutically effective amount of at least one donor cell.

Yet another embodiment of the invention pertains to a method of reducing rejection in a patient in need of a tissue-specific stem cell transplant. In this method, a hypothalamic-pituitary-gonadal (HPG) axis of the patient in need thereof is rebalanced by administering a therapeutically effective amount of at least one donor cell and administering a second stem cell that is tissue-specific to the patient.

Yet another embodiment of the invention relates to a method of preventing or slowing dyosis in a patient. In this method, a therapeutically effective amount of at least one physiological agent that regulates or increases the production of hormones produced by the gonads is administered to a patient.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The drawings presented are intended solely for the purpose of illustration and therefore, are neither desired nor intended to limit the subject matter of the disclosure to any or all of the exact details of construction shown, except insofar as they may be deemed essential to the claims.

DETAILED DESCRIPTION OF THE PREFERRED EMBODIMENTS

The present disclosure relates to a method of maintaining in balance or rebalancing, the hypothalamic-pituitary-gonadal (HPG) axis and preventing or reversing hypogonadism and accompanying symptoms and diseases. More particularly, embodiments of the present invention relates to a method for slowing, preventing or delaying senescence, preventing or treating a disease associated with senescence, and for increasing longevity. This is achieved by delivering donor cells into the human or animal body to increase the production and secretion of sex hormones into the circulation to levels near young adult reproductive levels, thereby reinitiating negative feedback on the hypothalamus and pituitary to rebalance the HPG axis hormone synthesis and secretion to levels near young adult reproductive levels. This in effect prevents dyotic (death) signaling that results from the dysregulation of the HPG axis. This will prevent and treat hypogonadism, prevent and treat symptoms associated with female reproductive endocrine dyscrasia and symptoms associated with male reproductive endocrine dyscrasia, and prevent or delay the onset of age-related diseases and extend longevity.

Figure 1A:
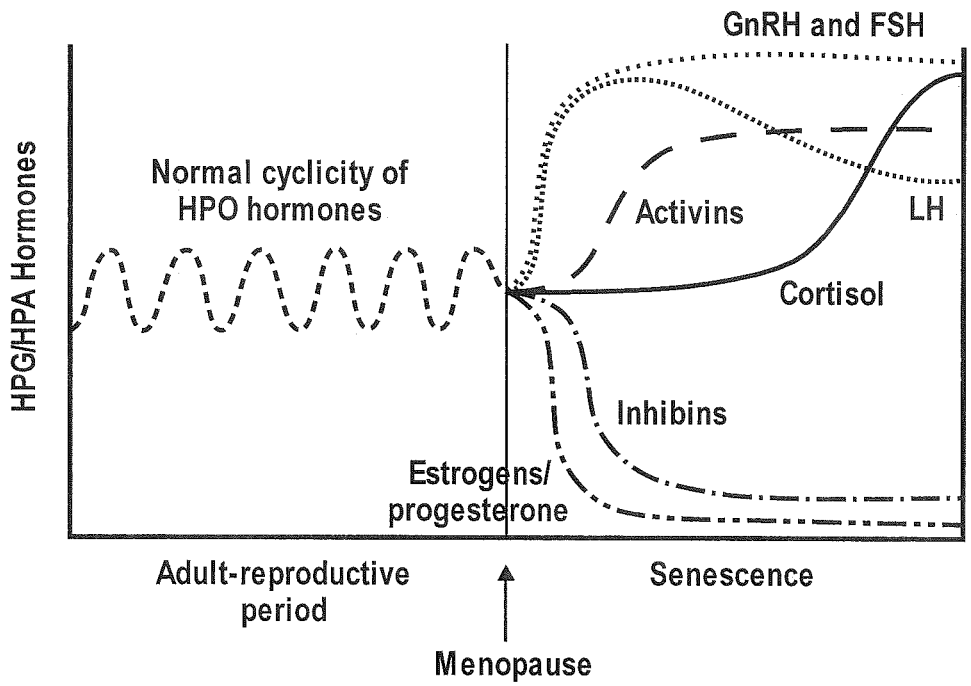
FIG. 1A illustrates the changes in hypothalamic-pituitary-gonadal hormones before and following menopause in women.
Figure 1B:
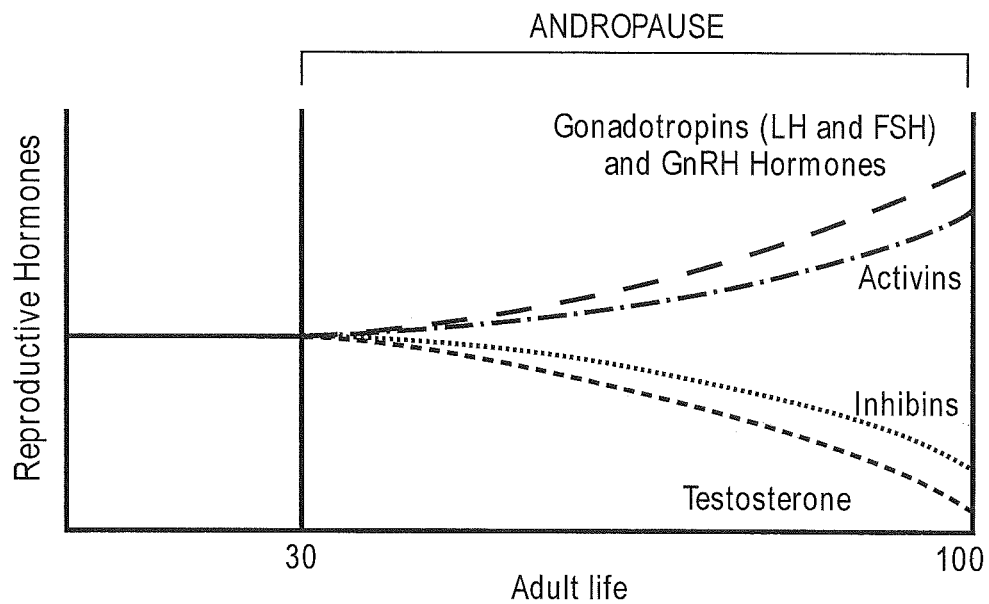
FIG. 1B illustrates the changes in hypothalamic-pituitary-gonadal hormones before and following andropause in men.
Figure 2:
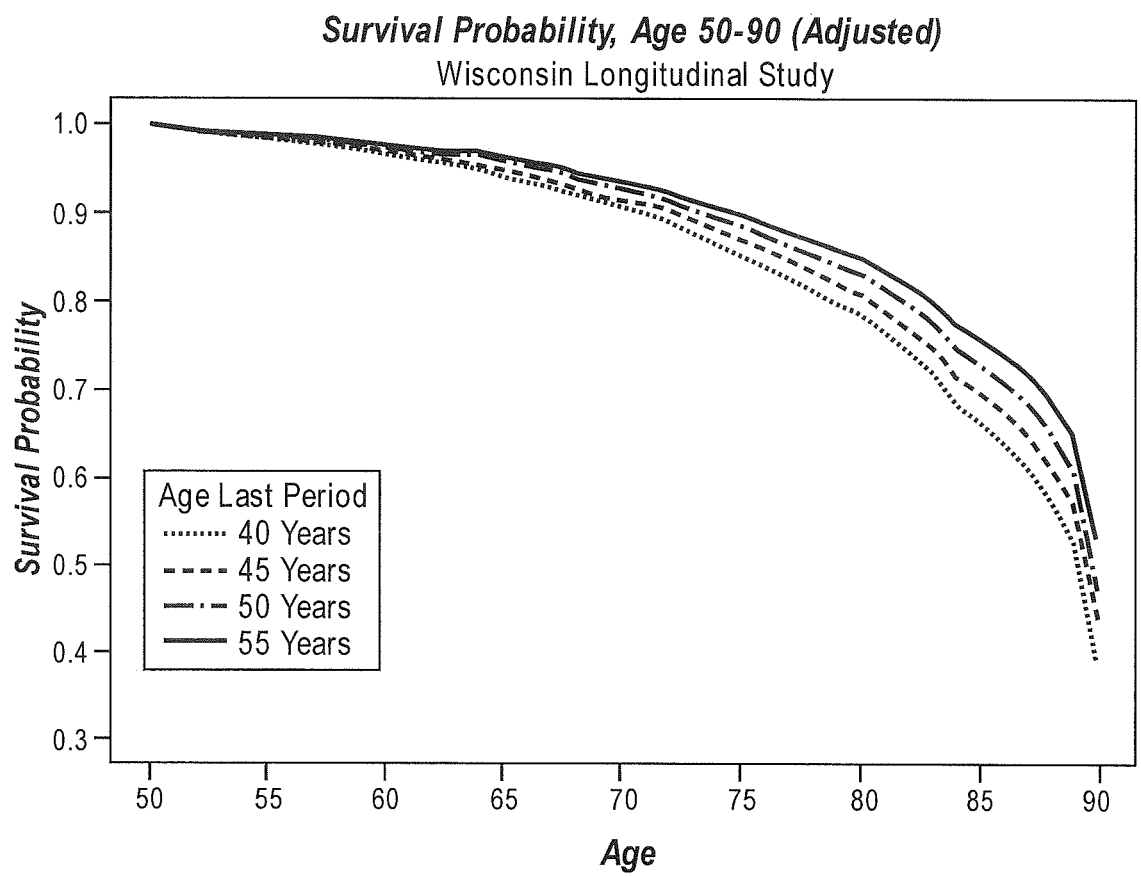
FIG. 2 illustrates the adjusted survival probability curves for women aged between 50 and 90 whose last menstrual period occurred at 40, 45, 50, or 55 years of age (Yonker et al. 2011).
Figure 3:
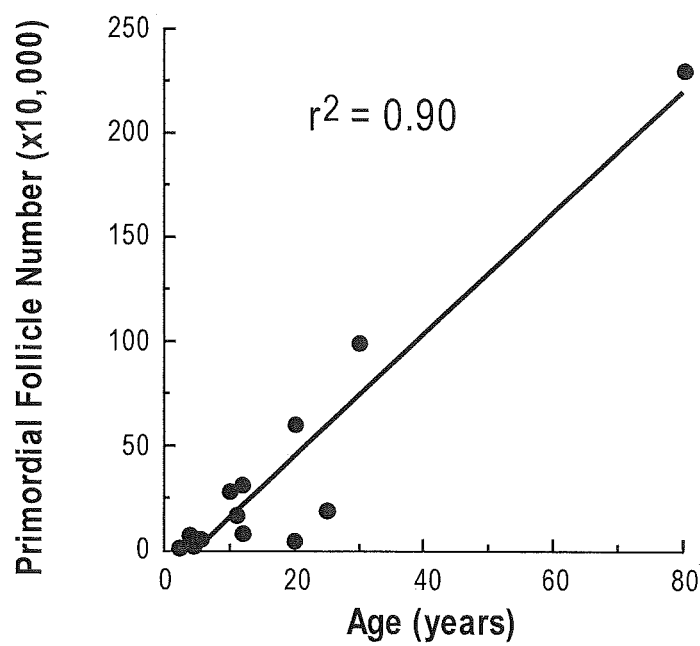
FIG. 3 illustrates primordial follicle number is closely correlated with longevity between species. Controlling for ovulation rate, for every additional 10,000 primordial follicles an animal is born with, there is an associated ~0.8% increase in longevity (Atwood et al., unpublished data).

We have determined that longevity between species is directly correlated with the number of ovarian primordial follicles that an animal is born with together with the rate at which they are used (FIG. 3; Atwood et al., unpublished data). Therefore, maintaining gonadal cells to prevent reproductive endocrine dyscrasia can offset senescent and age-related disease and increase longevity.

Preventing the dysregulation of the HPG axis by repopulating the ovaries with follicular cells, and the testes with Leydig, Sertoli and other support cells, will prevent hypogonadism and testosterone deficiency, symptoms thereof, and delay the onset of age-related diseases and extend longevity.

Restoring the HPG axis to balance (young adult reproductive levels) by repopulating the ovaries with follicular cells, and the testes with Leydig, Sertoli and other support cells, will reverse hypogonadism and testosterone deficiency syndrome, symptoms thereof, and delay the onset of age-related diseases and extend longevity.

Embodiments of the present invention relates to a method for preventing or reversing hypogonadism and increasing longevity by decreasing or preventing dyotic signaling via the rebalancing or maintenance of the HPG axis; by altering the blood and/or tissue levels, production, function, or activity of HPG axis hormones to be near the blood and/or tissue levels, production, function, or activity occurring during fetal life or at or around the height of the subject's reproductive function, in a subject, by administering donor cells that regulate the blood levels, production, function, or activity of any hormone produced by the gonads. This is a method for slowing, preventing or delaying senescence or treating or preventing a disease associated with senescence.

By "height of the subject's reproductive function" is meant that time (usually between 18-35 years of age) when subjects are most fertile and reproductive hormones are at their optimal for reproduction. "Subjects" may include humans or animals.

By "donor cell" is meant any cell that is undifferentiated (pluripotent, totipotent, multipotent, or induced pluripotent stem cells), differentiated or dedifferentiated that is to be transplanted into the body, or any organ of the body, so as to repopulate that organ or that is transplanted for the purpose of reestablishing the function of that organ or inducing a new function. The cells can be from the host organism (autologous cells) or from a donor organism (allogeneic cells).

Most cells are "terminally differentiated," meaning they no longer possess the ability to complete the "cell cycle," the process by which cells undergo chromosome replication and division to create two new daughter cells (Jacobsen 1991). Although terminally differentiated cells may be able to enter the cell cycle, they are unable to complete the process and usually undergo apoptosis (i.e., cell death) (Multani, et al. 2000). This can lead to cell loss and the development of a number of different diseases, including, but not limited to, Alzheimer's disease, Parkinson's disease, vascular dementia, frontal-temporal dementia, stroke, neoplasia, coronary heart disease, chronic obstructive pulmonary disease, osteoporosis, arthritis, diabetes mellitus II, etc. For example, evidence suggests that vascular smooth muscle cell proliferation leads to atherosclerosis (Lusis 2000). Cancers may result when terminally differentiated cells lose the protective ability to apoptose and are able to complete the cell cycle, resulting in abnormally increased cell proliferation (Hahn and Meyerson 2001).

Dysregulated HPG axis, dysregulated HPG signaling, endocrine dyscrasia and reproductive endocrine dyscrasia are used interchangeably to indicate the HPG axis (or other hormone axes) is not in balance, whether this be a result of aging, genetics or acquired.

"Dyosis" is the process by which dysregulated cell cycle signaling drives the biochemical and functional changes associated with senescence. Dysregulated cell cycle signaling, caused by altered mitogenic and differentiative stimuli, contributes to the development of the above diseases. By "dysregulated cell cycle signaling" is meant an increased frequency or rate of cells entering into the cell cycle, and/or inability of cells to complete the cell cycle. By "increased mitogenic stimulus" is meant an increase in the blood levels, production, function or activity of a mitogenic stimulus or a decrease in the blood levels, production, function, or activity of an anti-mitogenic stimulus. By "mitogenic stimulus" is meant a compound that acts as an impetus for cells to enter into the cell cycle, including, but not limited to, gonadotropin releasing hormone (GnRH), luteinizing hormone (LH), human chorionic gonadotropin (hCG), follicle-stimulating hormone (FSH), and activins. Throughout this application, the terms "upregulation of the cell cycle", "increased mitogenic stimulus" and "dysregulated cell cycle signaling" and "dyotic signaling" are used interchangeably. By "abnormally increased proliferation" is meant increased proliferation of cells that interferes with the normal function of the tissues and/or threatens the life or health of the subject.

"Menopause" is the cessation of a woman's reproductive ability due to the cessation of the primary functions of the ovaries. These primary functions include the inability to ovulate and release hormones which leads to reproductive (HPG axis) endocrine dyscrasia. Menopause is usually a natural change; it typically occurs in women in midlife, during their late 40s or early 50s, signaling the end of the fertile phase of a woman's life. However, in some women menopause can occur earlier or later. Menopause can also occur from premature ovarian failure or following bilateral oophorectomy (surgical menopause). Premature ovarian failure may be attributed to autoimmune disorders, thyroid disease, diabetes mellitus, polycystic ovary syndrome, being a carrier of the fragile X syndrome gene, chemotherapy and radiotherapy. The causes of the majority of spontaneous cases of premature ovarian failure are unknown, i.e. it is generally idiopathic. In the present disclosure, we are focusing on rebalancing all the hormones and not just estrogens and progesterone.

Premature ovarian failure, also known as premature ovarian insufficiency, primary ovarian insufficiency, premature menopause, hypergonadotropic hypogonadism, is the loss of function of the ovaries before age 40

"Andropause" is the gradual cessation of testicular function leading to endocrine dyscrasia and occurs in men starting at around 30 years of age (Atwood and Bowen 2011). Total testosterone declines by 0.9-1.6% per year after age 30, while free testosterone declines at a higher rate due to the concurrent increase in sex hormone binding globulin at an average rate of 1.3% per year, thereby compounding the effect of depleted total testosterone (Atwood and Bowen 2011; Feldman, et al. 2002; Gapstur, et al. 2002; Harman, et al. 2001; Liu, et al. 2007; T'Sjoen, et al. 2005; Travison, et al. 2007a; Travison, et al. 2007b). In the present disclosure, we are focusing on rebalancing all the hormones and not just testosterone.

"Hypogonadism" is a diminished functional activity of the gonads, pituitary or hypothalamus—that results in diminished sex hormone biosynthesis. Primary congenital forms of hypogonadism that impact ovarian function include being a carrier of the fragile X syndrome gene, Turner syndrome, Noonan syndrome, XY females with SRY gene-immunity, inborn errors of estrogen or progesterone synthesis, and estrogen or progestagen resistant states. Primary acquired forms of hypogonadism that impact ovarian function include autoimmune disorders, hysterectomy, oophorectomy, tuberculosis of the genital tract, thyroid disease, diabetes mellitus, prolonged GnRH therapy, chemotherapy, radiotherapy and various acute and chronic systemic disease. Primary congenital forms of hypogonadism that impact testicular function include Klinefelter's syndrome, Noonan's syndrome, inborn errors of testosterone synthesis, and androgen resistant states. Primary acquired forms of hypogonadism that impact testicular function include cryptorchidism (undescended testes), bilateral torsion, orchitis, orchidectomy (castration), gonadal toxins, including radiotherapy and chemotherapy, and various acute and chronic diseases.

Hypogonadotropic hypogonadism, also known as secondary or central hypogonadism, as well as gonadotropin-releasing hormone deficiency or gonadotropin deficiency (GD), is a condition which is characterized by hypogonadism due to an impaired secretion of gonadotropins, including follicle-stimulating hormone (FSH) and luteinizing hormone (LH), by the pituitary gland in the brain, and in turn decreased gonadotropin levels and a resultant lack of sex steroid production.

Secondary congenital forms of hypogonadism (hypogonadotropic hypogonadism) that impact testicular and/or ovarian function include Kallman syndrome, isolated GnRH deficiency, isolated LH deficiency, Prader-Willi syndrome, Turner syndrome, and Laurence-Moon-Biedl syndrome. Secondary acquired forms of hypogonadism that impact testicular and/or ovarian function include pituitary tumors and infarct, trauma, mumps, traumatic brain injury, children born to mothers who had ingested the endocrine disruptor diethylstilbestrol, opioid induced androgen deficiency (resulting from the prolonged use of opioid class drugs, e.g. morphine, oxycodone, methadone, fentanyl, hydromorphone), anabolic steroid-induced hypogonadism craniopharyngioma, hyperprolactemia (1° & 2°), hemochromatosis and neurosarcoid.

Late-onset hypogonadism (LOH, also referred to as age-associated testosterone deficiency syndrome (TDS)) is a clinical and biochemical syndrome associated with advancing age and characterized by symptoms and a deficiency in serum testosterone and inhibin levels (below the young healthy male reference range); ISA, ISSAM, EAU, EAA and ASA recommendations, 2009, International Society for Sexual Medicine (ISSM), 2010).

Testosterone deficiency syndrome (TDS) includes both severe hypogonadism described above and milder forms of hypogonadism whereby circulating testosterone concentrations have fallen by more than 30%. The most common form of TDS is age-related, driven by the yearly loss of 1-2% of key testicular cells (Sertoli and Leydig cells) that produce inhibins and testosterone, respectively. This loss starts at around 30 years of age, such that by age 50, gonadal hormone levels have fallen by 20-40%. Since all men start to lose gonadal cells around age 30, all men over 30 can be defined as having TDS, albeit with few symptoms (see below) until levels fall by 20-40%.

The terms andropause, hypogonadism, testosterone deficiency syndrome, late-onset hypogonadism, male menopause, hypergonadotropic hypogonadism, male climacteric, androgen decline in the aging male (ADAM), and aging male syndrome all involve age-related, congential or acquired reproductive endocrine dyscrasia in the male, and are used interchangeably in terms of HPG axis dysregulation (male reproductive endocrine dyscrasia).

The terms menopause, hypogonadism, premature ovarian failure, premature ovarian insufficiency, primary ovarian insufficiency, premature menopause, hypergonadotropic hypogonadism, all involve age-related, congential or acquired reproductive endocrine dyscrasia in the female, and are used interchangeably in terms of HPG axis dysregulation (female reproductive endocrine dyscrasia).

Hypogonadism, hypergonadotropic hypogonadism, andropause, menopause and related conditions may result in significant detriment in the quality of life and adversely affect the function of multiple organ systems. These conditions are associated with numerous symptoms and diseases of aging.

Symptoms associated with female reproductive endocrine dyscrasia include (Arakane, et al. 2011; Dreisler, et al. 2013; Freeman, et al. 2014; Freeman, et al. 2009; Freeman, et al. 2008; Freeman, et al. 2007; Llaneza, et al. 2011; Llaneza, et al. 2012; Monterrosa-Castro, et al. 2013; Monterrosa-Castro, et al. 2012; Ornat, et al. 2013; Perez-Lopez, et al. 2012; Pien, et al. 2008) vasomotor instability (hot flushes, night sweats, cold flashes), migraines, rapid heartbeat, and dysfunctional bleeding. Other symptoms include:

1. Urogenital (vaginal) atrophy—thinning of the membranes of the vulva, the vagina, the cervix, and also the outer urinary tract, along with considerable shrinking and loss in elasticity of all of the outer and inner genital areas, itching, dryness, watery discharge, urinary frequency, urinary continence, urinary urgency, increased susceptibility to inflammation and infection, for example vaginal candidiasis, and urinary tract infections.
2. Skeletal—back pain, joint pain, muscle pain, osteopenia and the risk of osteoporosis gradually developing over time, height loss.
3. Skin, soft tissue—breast atrophy, breast tenderness with and without swelling, decreased elasticity of the skin, formication (itching, tingling, burning, pins, and needles, or sensation of ants crawling), skin thinning and becoming drier, alopecia, increased weight gain, body fat and BMI, and frailty.
4. Psychological—depression and/or anxiety, fatigue, irritability, memory loss, and problems with concentration, mood disturbance, sleep disturbances, poor or light sleep, insomnia, and daytime sleepiness.
5. Sexual—dyspareunia, decreased libido and orgasm.

Symptoms associated with male reproductive endocrine dyscrasia include (Lincoln 2001; Sternbach 1998) vasomotor instability (hot flushes, night sweats, cold flashes), migraines, and rapid heartbeat. Other symptoms include:

1. Urogenital atrophy—small or shrinking testes, infertility; urinary frequency, urinary continence, urinary urgency.
2. Skeletal—back pain, joint pain, muscle pain, sarcopenia, osteopenia and the risk of osteoporosis gradually developing over time, height loss.
3. Skin, soft tissue—breast discomfort, gynecomastia, decreased elasticity of the skin, formication (itching, tingling, burning, pins, and needles, or sensation of ants crawling), skin thinning and becoming drier, alopecia, increased weight gain, body fat and BMI, and frailty.
4. Psychological—depression and/or anxiety, dysthymia, fatigue, decreased energy, motivation, self-confidence and work performance, irritability, hypersensitivity, anger, memory loss, and problems with concentration, mood disturbance, sleep disturbances, poor or light sleep, insomnia, and daytime sleepiness.
5. Sexual—decreased libido and activity, erectile dysfunction (decreased spontaneous erections), delayed sexual development.

In this specification, by "senescence" is meant any change in the function of an organism, or any of its tissues, that occurs concomitantly with a decline in reproductive function after the period of greatest reproductive function, which in humans typically corresponds to about 18 to 35 years of age. By "disease associated with senescence" is meant any disease, disorder, degeneration, tissue loss, or other unhealthy or abnormal condition caused by, linked to, or otherwise associated with senescence. Examples of diseases associated with senescence include, but are not limited to, artherosclerosis, brain cancer (including but are not limited to neuroma, anaplastic astrocytoma, neuroblastoma, glioma, glioblastoma multiforme, astrocytoma, meningioma, pituitary adenoma, primary CNS lymphoma, medulloblastoma, ependymoma, sarcoma, oligodendroglioma, medulloblastoma, spinal cord tumor, and schwannoma), polyps of the colon and colorectal cancer, myeloproliferative diseases (including but not limited to Hodgkin's disease, multiple myeloma, lymphoma, transient myeloproliferative disorder (TMD) (also known as transient myeloproliferative syndrome), congenital transient leukemia, congenital leukemoid reaction, transient leukaemoid proliferation, transient abnormal myelopoiesis, acute myeloid leukemia (AML), acute megakaryoblastic leukemia (AMKL) (also known as erythro-megakaryoblastic leukaemia); common B-lineage acute lymphoblastic leukemia (ALL), polycythemia, thrombocythemia, myelodysplastic syndromes, myelofibrosis, hypereosinophilic syndrome (HES), chronic lymphocytic leukemia, prolymphocytic leukemia, hairy-cell leukemia, chronic myelogenous leukemia, other leukemias, and other myelogenous cancers), osteoarthritis, osteoporosis, neoplasms, cataracts, macular degeneration, hearing loss, stroke, periodontal disease, osteopenia, peripheral neuropathy, COPD, hypertension, type 2 diabetes, sarcopenia, hypertension, primary pulmonary hypertension, congestive heart failure, left ventricular hypertrophy, cardiac valvular disease, esophagitis, esophageal stricture, gastroparesis, chronic pancreatitis, hypercholesterolemia, hypertriglyceridemia, cirrhosis of the liver, liver disease, Wilson's disease, kidney disease, hepatitis, cholelithiasis, cholecystitis, ulcerative colitis, inflammatory bowel disease, Crohn's disease, fibromyalgia, obesity, renal failure, proteinuria, gout, hyperuricemia, membranous nephropathy, polyarteritis nodosa, polymyalgia rheumatica, rheumatoid arthritis, progressive systemic sclerosis, spinal stenosis, spinal cord injury, migraine headaches, depression, major depression, anxiety, hair loss, baldness, male pattern baldness, sarcoidosis, Wegener granulomatosis, amyloidosis, dermatomyositis, graft versus host disease, systemic lupus erythematosus, seborrheic dermatitis, psoriasiform eczematous dermatitis, papulosquamous eczematous dermatitis, psoriasis, seborrheic keratosis, anagen effluvium, dysphagia, Barrett esophagus, achalasia, Chagas disease, facial neuropathy, trigeminal neuralgia, carpal tunnel syndrome, mitochondrial myopathies and encephalopathies, myasthenia gravis, traumatic brain injury, astrocytomas, oligodendrogliomas, meningiomas, schwannomas, pituitary adenomas, pineocytoma and pineoblastoma, primary central nervous system lymphoma, medulloblastomas, spinal cord tumors, paraneoplastic syndromes, anoxic encephalopathics, multiple sclerosis, Duchenne's muscular dystrophy, muscular dystrophy, transverse myelitis, Parkinson's disease, Lewy body disease, squamous cell carcinoma of the lung, adenocarcinoma of the lung, large cell carcinoma of the lung, small cell carcinoma of the lung, esophageal cancer, gastric cancer, pancreatic cancer, hepatocellular cancer, gallbladder carcinomas, colorectal cancer, Hodgkin's disease, non-Hodgkin's lymphoma, follicular lymphoma, small lymphocytic lymphoma, mantle cell lymphoma, marginal zone lymphoma, diffuse large cell lymphoma, Burkitt's and Burkitt's-like lymphoma, lymphoblastic lymphoma, peripheral T-cell lymphoma, large cell (T-cell and null) anaplastic lymphoma, primary anaplastic lymphoma, multiple myeloma, Ewing's sarcoma, chondrosarcomas, osteosarcomas, renal cell carcinoma, bladder carcinoma, testicular carcinoma, seminoma, nonseminoma, squamous cell carcinoma of the head and neck, salivary gland tumors, pneumoconioses, asbestosis, silicosis, coal worker's pneumoconiosis, berylliosis, malignant diffuse infiltrative lung disease, disease caused by pulmonary lymphangitic carcinomatosis, disease caused by alveolar cell carcinoma, chronic diffuse infiltrative lung disease of unknown etiology, sarcoidosis, idiophatic pulmonary fibrosis, desquamative interstitial pneumonia/respiratory bronchiolitis, interstitial lung disease, acute interstitial pneumonia, lymphocytic interstitial pneumonia, nonspecific interstitial pneumonia/fibrosis, bronchiolitis obliterans, Sjogren syndrome, mixed connective tissue disease, eosinophilic granuloma of the lung, allergic granulomatosis and anguitis, hypereosinophilic syndrome, osteoarthritis, spinal arthritis, ankylosing spondylitis, reactive arthritis (formerly known as Reiter syndrome), psoriatic arthritis, enteropathic arthritis, juvenile spondyloarthropathy, acne-associated arthritis, SAPHO (synovitis, acne, pustulosis, hyperostosis, osteitis) syndrome, Whipple disease, Paget's disease of bone, osteomalaci, decreased muscle mass, decreased skin elasticity, thinning of skin, decreased scalp hair growth, loss of subcutaneous collagen, decreased immune function, autoimmune disorders, decreased lung function, loss of arterial elasticity, urinary incontinence, degenerative disk disease, loss of renal function, brain damage associated with acute brain injury, tissue injury associated with acute tissue injury, Addison's disease, reduced reproductive capacity, reduced follicular number, reduced sperm motility, reduced semen volume, reduced sperm count and varicose veins.

Dysregulated cell cycle signaling (dyotic signaling), as occurs when the HPG axis becomes dysregulated with menopause or during andropause, and as occurs with congenital or acquired conditions described above, can lead to the aberrant re-entry of stem cells or post-mitotic (terminally differentiated) cells into the cell cycle. Such signaling leads to cell dysfunction and degeneration and altered cellular hormone levels that are not conducive to the normal functioning of tissues and the health of the subject. Such altered cell cycle signaling has been reported to lead to numerous diseases associated with senescence and aging, including but not limited to:

1. Cognitive decline/dementia. Elevated luteinizing hormone modulates the processing of amyloid-ß protein precursor and amyloid-ß deposition, promotes tau phosphorylation and drives aberrant neuronal cell division (Bowen, et al. 2004; McPhie, et al. 2003).
2. Decreased cerebrovascular function: Elevated gonadotropins increase the permeability of the blood-brain barrier, a precursor to stroke (Wilson, et al. 2008).
3. Osteoporosis. Elevated follicle-stimulating hormone increases the ratio of osteoclasts to osteoblasts, resulting in bone resorption and osteoporosis (Sun, et al. 2006).
4. Immune dysregulation. Dyotic signaling leads to suppressed immune function.
5. Cancer. Dyotic signaling leads to suppressed immune function, promoting the development of neoplasia (Chahal and Drake 2007; Gameiro and Romao 2010; Gameiro, et al. 2010).
6. Diabetes mellitus. Dyotic signaling alters fuel metabolism leading to obesity, insulin insensitivity, metabolic syndrome and diabetes mellitus type II (Atwood and Bowen 2007; Clark, et al. 2012).
7. Rheumatoid arthritis. Elevated LH and FSH promote the onset and exacerbation of rheumatoid arthritis (Kass et al., 2010).

The invention encompasses a method of preventing or reversing the dysregulation of the HPG axis by repopulating the ovaries with follicular cells, and the testes with Leydig, Sertoli and other support cells. This will prevent and treat hypogonadism, prevent and treat symptoms associated with female reproductive endocrine dyscrasia and symptoms associated with male reproductive endocrine dyscrasia, and prevent and delay the onset of age-related diseases and extend longevity.

The invention encompasses a method of restoring the HPG axis to balance (young adult reproductive levels) by repopulating the ovaries with follicular cells, and the testes with Leydig, Sertoli and other support cells. This will reverse hypogonadism, prevent and treat symptoms associated with female reproductive endocrine dyscrasia and symptoms associated with male reproductive endocrine dyscrasia, and prevent and delay the onset of age-related diseases and extend longevity.

The invention further encompasses a method of inhibiting inflammation such as decreasing the expression of tumor necrosis factor (TNF), in a subject, by administering donor cells that lead to a rebalancing of the HPG axis.

Thus, the present invention encompasses reversing the degenerative serum hormonal milieu back to one that allows the appropriate growth and development of cells for the normal maintenance of tissue structure and function in the body. Rebalancing the endocrine HPG axis will allow for the rebalancing of the tissue specific 'mini-HPG' axes present in tissues throughout the body (Meethal et al. 2009b). This will rebalance reproductive hormone signaling to cells in all tissues of the body.

This can be achieved by injecting into a subject donor cells that can repopulate the gonads with cell types capable of producing reproductive hormones required to balance the HPG axis. For male subject, donor cells capable of differentiating into germ cells (spermatogonia, spermatocytes, spermatids and spermatozoon), Sertoli cells, myoid cells, Leydig cells, stromal cells, macrophage cells and/or epithelial cells and integrating into the tissue to restore function. For female subject, donor cells capable of differentiating into germ cells (oogonial stem cells), granulosa cells, cumulus cells, thecal cells, stromal cells, epithelial cells, macrophage cells and/or oocyte cells, and integrating into the tissue to restore function.

The differentiation of donor cells into more than one gonadal cell type is required to allow complete rebalancing of the axis. For example, while Leydig cells primarily produce androgens, Sertoli cells produce large quantities of inhibins, both of which are required for HPG axis rebalancing in males.

An embodiment of the present invention includes administering, to a subject, donor cells that decrease or regulate the blood levels, production, function or activity of gonadal hormone to be near the blood levels, production, function or activity occurring during fetal life or at or around the height of the subject's reproductive period, which in humans usually corresponds to about 18 to 35 years of age.

In another embodiment, the present invention encompasses administering, to a subject, donor cells that decrease or regulate the blood levels, production, function or activity of kisspeptin, GnRH, LH or FSH to be approximately as low as possible without significant adverse side effects, preferably to be undetectable or nearly undetectable by conventional detection techniques known in the art, which, at the present time, is less than 0.7 mIU/mL for both LH and FSH. In another embodiment, the present invention encompasses administering, to a subject, donor cells that regulate the function or activity of activin to be approximately as low as possible without significant adverse side effects, preferably to be undetectable or nearly undetectable by conventional detection techniques known in the art. In another embodiment, the present invention encompasses administering donor cells that increase or regulate the blood levels, production, function, or activity of inhibin, follistatin, myostatin or BMP4 to be approximately as high as possible without significant adverse side effects.

In other embodiments of the present invention, the blood levels, production, function or activity of gonadal hormones are continuously regulated, by monitoring the blood levels, production, function or activity and making adjustments to the donor cell or donor cells being administered via a feedback control system.

Embodiments of the present invention include administration of one or more stem or differentiated cell types that can be used to increase or regulate the blood and/or tissue levels, production, function or activity of gonadal hormones. Studies have shown that increasing the levels of circulating sex steroids and inhibins will result in significant decreases in GnRH, LH and FSH levels and a rebalancing of the HPG axis (Hayes, et al. 1998; Thorner et al. 1998; Ying 1988). Through a negative feedback loop, the presence of sex steroid hormones such as estrogen, testosterone or progesterone signals the hypothalamus to decrease the secretion of GnRH (Gharib, et al. 1990; Steiner, et al. 1982). The subsequent decrease in GnRH decreases the secretion of LH and FSH (Thorner et al. 1998). For example, sex steroids, inhibins and follistatin have been shown to provide negative feedback regulation of GnRH and FSH synthesis and secretion (Bagatell, et al. 1994; Boepple, et al. 2008; Dubey, et al. 1987; Hayes, et al. 2001b; Illingworth, et al. 1996; Lambert-Messerlian, et al. 1994; Marynick, et al. 1979; Pitteloud, et al. 2008a, b; Schnorr, et al. 2001; Sherins and Loriaux 1973; Winters, et al. 1979a; Winters, et al. 1979b) while sex steroids appear to primarily provide negative feedback for the regulation of GnRH and LH synthesis and secretion (Bagatell et al. 1994; Hayes, et al. 2001a; Santen 1975; Schnorr et al. 2001; Veldhuis, et al. 1992). In females, sex steroids, inhibins and follistatin have been shown to provide negative feedback regulation of FSH (le Nestour, et al. 1993; Welt, et al. 1997) and LH (Jaffe and Keye 1974, 1975; Jaffe, et al. 1976; Keye and Jaffe 1974, 1975, 1976; Liu and Yen 1983; Taylor, et al. 1995; Young and Jaffe 1976) synthesis and secretion.

Embodiments of the present invention also encompass rebalancing of the HPG axis such that the axis and related hormonal concentrations are balanced for that person. The production of sex hormones by donor cells is expected to be different for different individuals in order to reach optimal balancing of that person's HPG axis. Thus, the circulating and tissue concentrations of sex hormones in one person's balanced HPG axis is expected to be different to that of another person whose axis is also balanced.

Embodiments of the present invention also encompass the minute-to-minute, hour-to-hour and day-to-day variations in HPG axis hormone production to allow the axis to remain in balance.

Embodiments of the present invention also encompass returning the ratios of sex hormones back to near the ratios occurring during fetal life or at or near the time of greatest reproductive function of the subject. For example, the ratio of testosterone:FSH during the male reproductive period is ~11 (6.5 ng/mL:0.6 ng/mL), while that during the post-reproductive period (post-menopause) is ~1 (2.3 ng/mL:2.3 ng/mL). In this example, treatment would aim to return the ratio of these hormones back to 11. Further embodiments to this invention would encompass returning all the sex hormone ratios back to those during fetal life or at the time of greatest reproductive function of the subject.

Embodiments of the present invention also encompass administration of purified and mixed donor cell populations derived from the tissues of an individual who will receive the donor cells.

Embodiments of the present invention also encompass administration to an individual purified and mixed donor cell populations derived from multiple tissues of one or more individuals.

Embodiments of the present invention encompass administration of autologous or allogenic donor cell populations into the gonads for the prevention or treatment of hypogonadism, hypergonadotropic hypogonadism, andropause, menopause and related conditions, and for the prevention and treatment of diseases associated with senescence and aging.

Embodiments of the present invention also encompass administration of donor cell populations into the gonads prior to administration of donor cell populations (e.g. stem cell therapy, iPS therapy, or implantation/injection of differentiated cells including stem cells that have been differentiated in vitro) into other tissues of the body. Such a method allows for rebalancing the HPG axis so that the 'toxic environment of dyotic signaling' is reversed in order to allow for donor cells transplanted into other tissues to differentiate appropriately, integrate into the tissue and restore function.

In other embodiments of the invention, donor cell recipients may receive supplemental gonadal hormones, GnRH agonists/antagonists, an LH/FSH-inhibiting agent, an activin-inhibiting agent, an inhibin-promoting agent, and/or a follistatin-promoting agent.

According to embodiments of the present invention, administration of GnRH agonists/antagonists, LH/FSH-inhibiting agents, activin-inhibiting-agents, inhibin-promoting agents, follistatin-promoting agents, or sex steroids, including those listed above, can be oral or by injection, inhalation, patch, or other effective means. According to embodiments of the present invention, the dosage of GnRH agonists/antagonists, LH/FSH-inhibiting agents, activin-inhibiting agents, inhibin-promoting agents, follistatin-promoting agents, or sex steroids, including those identified above, will be a therapeutically effective amount, sufficient to decrease or regulate the blood and/or tissue levels, production, function or activity of GnRH, LH or FSH, or to decrease or regulate the function or activity of activin or to increase or regulate the blood and/or tissue levels, production, function or activity of inhibin or follistatin, to the desired blood and/or tissue levels, production, function or activity. According to other embodiments of the invention, administration of LH/FSH-inhibiting agents, activin-inhibiting agents, inhibin-promoting agents, follistatin-promoting agents, or sex steroids, including those identified above, can be in a single dose, multiple doses, in a sustained release dosage form, in a pulsatile form, or in any other appropriate dosage form or amount. Administration prior to treatment with cells is preferred, but can occur during or after administration of cells. The duration of treatment could range from a few days or weeks to the remainder of the patient's life.

In addition to treating neurodegenerative diseases, the administration of GnRH agonists/antagonists, LH/FSH-inhibiting agents, activin-inhibiting agents, inhibin-promoting agents, follistatin-promoting agents, sex steroids, or other agents that decrease dysregulated cell cycle signaling, as described above, is expected to be beneficial in the treatment of aging and diseases where cell replenishment is required in order to repopulate a tissue to regain function or establish a new function, in accordance with the present invention.

EXAMPLES

Example 1

Adult stem mesenchymal stem cells (MSCs) (or bone marrow strornal cells), are pluripotent cells that have the ability to differentiate into cells of all three germ layers (Ratajczak, et al. 2008). MSCs injected into the testes localize to the testicular interstitium and seminiferous tubules and differentiate into Leydig cells and spermatogonia/spermatocytes, respectively (Lo, et al. 2004; Yazawa, et at 2006). Stem cells injected into the ovaries increase follicle numbers (Abd-Allah, et al. 2013). Hormonal factors secreted within the gonads direct the differentiation and integration of such stem cells for the replenishment of germ cells, Leydig, Sertoli and other cells in the testes, and replenishment of follicular cells (germ cells, granulosa, thecal and other cells) in the ovaries. Hormones secreted by the transplanted cells and their progeny in turn rebalance the HPG axis.

In the case of a human male or female, MSCs are isolated from 1) bone, the femur and/or tibia (Tuli, et al. 2003a; Tuli, et al. 2003b), 2) umbilical cord blood (Hayward, et al. 2013; Malgieri, et al. 2010), 3) Wharton's jelly (Hayward et al. 2013), 4) skin (Manini, et al. 2011) or 5) adipose tissue (Kuhbier, et al. 2010; Manini et al. 2011; Tholpady, et al. 2003; Zhu, et al. 2013; Zuk, et al. 2001). Cells are then subjected to flow cytometry to isolate MSC that are then injected (10,000-1 billion cells/treatment) into the interstitium of one or both testes or ovaries of the donor. In the testes, cells can be injected into the seminal vesicle lobules, septa, tunica albuginea, straight tubule, rete testes, efferent ductile and/or epididymis. In the ovary, cells can be injected into the ovarian cortex. If the number of isolated MSCs is insufficient, MSCs are expanded in culture first prior to injection into the gonads.

This technique may be performed autologously, i.e. isolating cells from the same individual who will receive the cells; allogeneically, i.e. cells isolated from one individual are injected into another individual (human or animal); or both autologously and allogeneically, i.e. isolated cells from the recipient and from another individual(s) are injected into the recipient.

In this example, MCSs, from which gonadal tissues are derived during embryogenesis, are purified from tissues other than the gonads and then injected into the gonads.

MSCs in a suitable buffer, or encapsulated in a hydrogel or other matrix (e.g. fibrin, collagen) prior to injection, may be injected into the gonads (testes or ovaries). Injection may be via a catheter. MSCs in this example are capable of differentiating into all relevant gonadal cell types upon injection into the gonads.

This technique can be used on humans, animals and plants with a reproductive hormone axis.

The concentration of circulating reproductive hormones in the individual can be measured before and after the injection of cells to confirm that injected cells are producing hormones and rebalancing the HPG axis. Tissue concentrations of reproductive hormones can be measured in tissues to confirm that the hormones of the 'mini-HPG-axis in that tissue have rebalanced (returned to young adult reproductive concentrations). If the HPG axis has not completely rebalanced, a second or subsequent injection can be given until such time as the HPG axis is balanced and dyotic signaling has decreased. This provides a preventative and treatment for hypogonadism (primary) and of age-related reproductive endocrine dyscrasia.

Example 2

MSCs or other stem cell populations are differentiated in vitro into discrete precursor or differentiated cell types including germ cells (spermatogonia, spermatocytes, spermatids and spermatozoon), Sertoli cells, myoid cells, Leydig cells, stromal cells, macrophage cells and/or epithelial cells in the case of the male; or germ cells (oogonial stem cells), granulosa cells, cumulus cells, thecal cells, stromal cells, epithelial cells, macrophage cells and/or oocyte cells\, in the case of the female, and one or preferably more of these cell types are injected into the gonads and/or other tissues and circulating and tissue sex hormone concentrations measured as in the methods described in Example 1, for rebalancing of the HPG axis.

Example 3

Adult testicular cells such as Sertoli cells, Leydig cells and germ cells can be differentiated from MSCs following transfection with members of the nuclear receptor family, SF-1 or liver receptor homolog-1 (LRH-1), and treatment with 8-bromoadenosine-cAMP (Yazawa et al. 2006). One or preferably both of these cell types are injected into the male gonads and/or other tissues neat or in matrices via methods described in Example 1 and circulating and tissue sex hormone concentrations measured as in the methods described in Example 1, for rebalancing of the HPG axis. Cells may be autologous or allogeneic. In a derivation of this method, MSC or other cell types are treated with differentiation factors as described in Example 3, and injected within 24 h into the testes via methods described in Example 1. In another derivation of this method, MSC or other cell types are imbedded in a matrix impregnated with differentiation factors and injected into the testes via methods described in Example 1.

Adult granulosa, cumulus, thecal and germ cells can be isolated from adult ovaries following tituration, percoll gradients and/or flow cytometry (Sittadjody, et al. 2013) and one or preferably more of these cell types injected into the female gonads and/or other tissues and circulating and tissue sex hormone concentrations measured as in the methods described in Examples 1 and 3, for rebalancing of the HPG axis.

Example 4

Donor cells derived from the gonads of the recipient are differentiated into discrete precursor or differentiated cell types including germ cells (spermatogonia, spermatocytes, spermatids and spermatozoon), Sertoli cells, myoid cells, Leydig cells, stromal cells, macrophage cells and/or epithelial cells in the case of the male; or germ cells (oogonial stem cells), granulosa cells, cumulus cells, thecal cells, stromal cells, epithelial cells, macrophage cells and/or oocyte cells, in the case of the female, and one or preferably more of these cell types are injected into the gonads and/or other tissues and circulating and tissue sex hormone concentrations measured as in the methods described in Example 1, for rebalancing of the HGP axis.

Example 5

Donor cells derived from the gonads of the recipient are treated with demethylation agents to allow for epigenetic silencing. As in the methods described in Example 1, these cells are injected into the gonads and/or other tissues and circulating and tissue sex hormone concentrations measured.

Example 6

Cells derived from somatic-cell nuclear transfer (SCNT) into an enucleated oocyte (Byrne, et al. 2007) can be cultured to produce sufficient cell numbers to be injected into either one or both of the gonads, and/or injected into the circulation, and/or other tissues of the body and circulating and tissue sex hormone concentrations measured as described in Example 1 to rebalance the HPG axis. The nucleus used for SCNT may be from the same individual who is receiving the injection, or from a different individual than who is receiving the injection. The enucleated oocyte may be from the same individual who is receiving the injection, or from a different individual than who is receiving the injection.

Example 7

This Technique can be Used on Humans, Animals and Plants with a Reproductive Hormone Axis Induced pluripotent stem (iPS) cells created from the recipient or another donor can be cultured to produce sufficient cell numbers to be injected into either one or both of the gonads, and/or injected into the circulation, and/or other tissues of the body and circulating and tissue sex hormone concentrations measured as described in Example 1 to rebalance the HPG axis. Differentiated cells such as fibroblasts, umbilical cord fibroblasts stomach, hepatocytes, lymphocytes, prostatic cells and other adult differentiated cells can be Obtained by various techniques known in the field and reprogrammed into iPS cells via the following techniques also known in the field.

Generation of iPSCs

Reprogramming with Lentiviral Transduction

Three plasmid vectors of lentiviral reprogramming: FUW-tetO-lox-hO2S, FUW-tetO-lox-hM2K, and FUW-tetO-lox-hN2L are constructed. Expression cassettes of human POU5F1-internal ribosome entry site 2 (IRES2)-SOX2 (O2S) and MYC-IRES2-KLF4 (M2K) of pEP4 EO2S EM2K (Addgene, #20923) (Yu, et al. 2009) are used for the O2S and M2K cassettes. Pseudovirus is produced in 293FT cells by transfection with each lentiviral vector (O2S, M2K, N2L) and the reverse tetracycline transactivator expression plasmid, FUW-M2rtTA (Addgene, plasmid 20342) (Hockemeyer, et al. 2008) along with the VSV-G envelope (pMD2.G) and packaging vector (psPAX2) (Ezashi, et al. 2009). Two consecutive infections are introduced into the target cell or interest ($1 \times 10^5$ cells) in the presence of 12 µg/ml hexadimethrine bromide (polybrene, Sigma, St. Louis, Mo.). During the infection stage, the cells are cultured for 48 h by adding a mixture of the four titered pseudoviruses (multiplicity of infection); O2S (30.8), M2K (17.5), N2L (18.2) and rtTA (20.7) to the culture medium. On day 4 after infection, cells are dispersed with trypsin and then expanded. Cells are tested for pluripotency and can then be used for treatment.

Reprogramming with Episomal Plasmids

Episomal vectors carrying the reprogramming genes SOX2, KLF4, POU5F1, LIN28, p53 and MYCL (combined episomal plasmids; Addgene #27077, 27078 and 27080) are electroporated into $1-6 \times 10^5$ cells using a Nucleofector II device (Lonza, Basel, Switzerland) and Amaxa NHDF Nucleofector kit (Lonza). After 20 days, colonies resembling human ESC are mechanically isolated and expanded in mTeSRl medium (Gallego et al. 2010; Ludwig, et al. 2006; Porayette, et al. 2009) (StemCell Technologies, Vancouver, Canada) on a Matrigel (BD Bioscience, San Jose, Calif.) coated substratum. Cells are tested for pluripotency and can then be used for treatment.

Example 8

The patient is pre-treated with agents to lower dyotic signaling, such as GnRH agonists/antagonists and/or sex steroid supplementation (e.g. testosterone in males; estradiol and progesterone in females), prior to treatment with donor cells as outlined in Examples 1-7 to aid in the repopulation of gonadal cells.

Pre-treatment of patients described above is performed prior to the injection of donor cells into non-gonadal tissues or the circulation, and tissue regeneration and function monitored.

Example 9

The above methods in Examples 1-8 can be utilized to rebalance the HPG axis and reverse or prevent dyotic signaling in tissues, thereby allowing for a more conducive environment for innate tissue regeneration or regeneration aided by treatment with donor cells. The methods from Examples 1-8 can be performed on patients, circulating and tissue sex hormone concentrations measured to confirm the HPG axis is rebalanced and that dyotic signaling has decreased, prior to the injection of donor cells into specific tissues or the circulation, and tissue regeneration and function monitored. As one example, the method of Example 1 can be used to decrease dyotic signaling to the brain, and donor cells (e.g. neural stem cells, iPS cells or differentiated neural cells) injected into a dysfunctioning region(s) of the brain.

Example 10

These techniques can be used to treat hypogonadotropic hypogonadism (secondary hypogonadism), a condition characterized by hypogonadism due to an impaired secretion of gonadotropins, including FSH and LH, by the pituitary gland in the brain, and in turn decreased gonadotropin levels and a resultant lack of sex steroid production. Pituitary cell types such as gonadotrophs, corticotrophs, thyrotrophs, lactotrophs and adipose generated by way of Examples 1-3, 5-7, and from pituitary tissue, can be cultured to produce sufficient cell numbers to be injected into the pituitary, and/or injected into the circulation, and/or other tissues of the body to rebalance the HPG axis as described in Examples 1-7 with or without pre-treatment of patients described in Example 8. Circulating and tissue sex hormone concentrations measured as described in Example 1 are performed to confirm rebalancing of the HPG axis. Conditions and diseases treated by this method include secondary congenital forms of hypogonadism (hypogonadotropic hypogonadism): Kallman syndrome, isolated GnRH deficiency, isolated LH deficiency, Prader-Willi syndrome, Turner syndrome, and Laurence-Moon-Biedl syndrome; and secondary acquired forms of hypogonadism: pituitary tumors and infarct, trauma, mumps, traumatic brain injury, children born to mothers who had ingested the endocrine disruptor diethylstilbestrol, opioid induced androgen deficiency (resulting from the prolonged use of opioid class drugs, e.g. morphine, oxycodone, methadone, fentanyl, hydromorphone), anabolic steroid-induced hypogonadism craniopharyngioma, hyperprolactemia (1° & 2°), hemochromatosis and neurosarcoid.

Example 11

The above techniques also can be used to treat other dysregulated hormone axes of the body, including conditions and diseases that dysregulate the hypothalamic-pituitary-adrenal axis (e.g. adrenal insufficiency, Cushing's syndrome, Addison disease), alimentary system hormone axes, placental hormone axes, calcium regulatory axes, salt regulatory axes, thermoregulatory axes and thyroid hormone axes Example 12

The above techniques in Examples 1-11 can be used to treat animals such as stud bulls or horses, pets and members of rare and endangered species in order to restore hormone balance and improve or maintain health and lifespan.

CONCLUSION

While various embodiments of the present invention have been described above, it should be understood that they have been presented by way of example only, and not by limitation. For example, the present invention is not limited to the stem or differentiated cells illustrated or described, the methods of injection, the hormones produced by the cells, or the injected tissues illustrated or described. In another example, although some cells and techniques described herein are related to humans, the present invention is not limited to humans, but rather, includes all reproductively viable organisms. As such, the breadth and scope of the present invention should not be limited to any of the above-described exemplary embodiments, but should be defined only in accordance with the following claims and their equivalents.

REFERENCES

Abd-Allah S H, Shalaby S M, Pasha H F, El-Shal A S, Raafat N, Shabrawy S M, Awad H A, Amer M G, Gharib M A, El Gendy E A, et al. 2013 Mechanistic action of mesenchymal stem cell injection in the treatment of chemically induced ovarian failure in rabbits. *Cytotherapy* 15 64-75.

Arakane M, Castillo C, Rosero M F, Penafiel R, Perez-Lopez F R & Chedraui P 2011 Factors relating to insomnia during the menopausal transition as evaluated by the Insomnia Severity Index. *Maturitas* 69 157-161.

Arantes-Oliveira N, Apfeld J, Dillin A & Kenyon C 2002 Regulation of life-span by germ-line stem cells in *Caenorhabditis elegans*. *Science* 295 502-505.

Atwood C & Vadakkadath Meethal S 2011a Gonadotropins and Progestogens: Obligatory Developmental Functions during Early Embryogenesis and their Role in Adult Neurogenesis, Neuroregeneration, and Neurodegeneration. In *Hormones in Neurodegeneration, Neuroprotection and Neurogenesis*, pp 305-319. Ed AGaS Mellon. Weinheim, Germany: WILEY-VCH Verlag GmbH & Co.

Atwood C & Vadakkadath Meethal S 2011b Human Embryonic Stem Cells as a Model System for Understanding Early Human Embryogenesis and Age-related Diseases. In *Embryonic Stem Cells: The Hormonal Regulation of Pluripotency and Embryogenesis*, pp 251-270. Ed CS Atwood. Rijeka, Croatia: InTech.

Atwood C S & Bowen R L 2007 Metabolic clues regarding the enhanced performance of elite endurance athletes from orchiectomy-induced hormonal changes. *Medical hypotheses* 68 735-749.

Atwood C S & Bowen R L 2011 The reproductive-cell cycle theory of aging: an update. *Experimental Gerontology* 46 100-107.

Atwood C S, Meethal S V, Liu T, Wilson A C, Gallego M, Smith M A & Bowen R L 2005 Dysregulation of the hypothalamic-pituitary-gonadal axis with menopause and andropause promotes neurodegenerative senescence. *J Neuropathol Exp Neurol* 64 93-103.

Bagatell C J, Dahl K D & Bremner W J 1994 The direct pituitary effect of testosterone to inhibit gonadotropin secretion in men is partially mediated by aromatization to estradiol. *Journal of andrology* 15 15-21.

Belanger A, Candas B, Dupont A, Cusan L, Diamond P, Gomez J L & Labrie F 1994 Changes in serum concentrations of conjugated and unconjugated steroids in 40- to 80-year-old men. *J Clin Endocrinol Metab* 79 1086-1090.

Boepple P A, Hayes F J, Dwyer A A, Raivio T, Lee H, Crowley W F, Jr. & Pitteloud N 2008 Relative roles of inhibin B and sex steroids in the negative feedback regulation of follicle-stimulating hormone in men across the full spectrum of seminiferous epithelium function. *The Journal of clinical endocrinology and metabolism* 93 1809-1814.

Bowen R L & Atwood C S 2004 Living and dying for sex. A theory of aging based on the modulation of cell cycle signaling by reproductive hormones. *Gerontology* 50 265-290.

Bowen R L, Verdile G, Liu T, Parlow A F, Perry G, Smith M A, Martins R N & Atwood C S 2004 Luteinizing hormone, a reproductive regulator that modulates the processing of amyloid-beta precursor protein and amyloid-beta deposition. *The Journal of biological chemistry* 279 20539-20545.

Byrne J A, Pedersen D A, Clepper L L, Nelson M, Sanger W G, Gokhale S, Wolf D P & Mitalipov S M 2007 Producing primate embryonic stem cells by somatic cell nuclear transfer. *Nature* 450 497-502.

Cargill S L, Carey J R, Muller H G & Anderson G 2003 Age of ovary determines remaining life expectancy in old ovariectomized mice. *Aging Cell* 2 185-190.

Can B R 1998 Williams Textbook of Endocrinology. pp 751-817. Ed F D Wilson J D, Kronenberg H M, Larsen P R. Philadelphia Pa.: WB Saunders Co.

Cash J N, Angerman E B, Keutmann H T & Thompson T B 2012 Characterization of follistatin-type domains and their contribution to myostatin and activin A antagonism. *Molecular endocrinology* 26 1167-1178.

Chahal H S & Drake W M 2007 The endocrine system and ageing. *The Journal of pathology* 211 173-180.

Clark I, Atwood C, Bowen R, Paz-Filho G & Vissel B 2012 Tumor Necrosis Factor-Induced Cerebral Insulin Resistance in Alzheimer's Disease Links Numerous Treatment Rationales. *Pharmacological reviews*.

de Bruin J P, Gosden R G, Finch C E & Leaman B M 2004 Ovarian aging in two species of long-lived rockfish, Sebastes aleutianus and S. alutus. *Biol Reprod* 71 1036-1042.

DeKretser D M, Hedger M P, Loveland K L & Phillips D J 2002 Inhibins, activins and follistatin in reproduction. *Hum. Reprod.* Update 8 529-541.

Dreisler E, Poulsen L G, Antonsen S L, Ceausu I, Depypere H, Erel C T, Lambrinoudaki I, Perez-Lopez F R, Simoncini T, Tremollieres F, et al. 2013 EMAS clinical guide: assessment of the endometrium in peri and postmenopausal women. *Maturitas* 75 181-190.

Dubey A K, Zeleznik A J & Plant T M 1987 In the rhesus monkey (*Macaca mulatta*), the negative feedback regulation of follicle-stimulating hormone secretion by an action of testicular hormone directly at the level of the anterior pituitary gland cannot be accounted for by either testosterone or estradiol. *Endocrinology* 121 2229-2237.

Ezashi T, Telugu B P, Alexenko A P, Sachdev S, Sinha S & Roberts R M 2009 Derivation of induced pluripotent stem cells from pig somatic cells. *Proceedings of the National Academy of Sciences of the United States of America* 106 10993-10998.

Feldman H A, Longcope C, Derby C A, Johannes C B, Araujo A B, Coviello A D, Bremner W J & McKinlay J B 2002 Age trends in the level of serum testosterone and other hormones in middle-aged men: longitudinal results from the Massachusetts male aging study. *The Journal of clinical endocrinology and metabolism* 87 589-598.

Freeman E W, Sammel M D, Boorman D W & Zhang R 2014 Longitudinal pattern of depressive symptoms around natural menopause. *JAMA psychiatry* 71 36-43.

Freeman E W, Sammel M D & Lin H 2009 Temporal associations of hot flashes and depression in the transition to menopause. *Menopause* 16 728-734.

Freeman E W, Sammel M D, Lin H, Gracia C R & Kapoor S 2008 Symptoms in the menopausal transition: hormone and behavioral correlates. *Obstetrics and gynecology* 111 127-136.

Freeman E W, Sammel M D, Lin H, Gracia C R, Pien G W, Nelson D B & Sheng L 2007 Symptoms associated with menopausal transition and reproductive hormones in midlife women. *Obstetrics and gynecology* 110 230-240.

Gallego M J, Porayette P, Kaltcheva M M, Bowen R L, Vadakkadath Meethal S & Atwood C S 2010 The pregnancy hormones human chorionic gonadotropin and progesterone induce human embryonic stem cell proliferation and differentiation into neuroectodermal rosettes. *Stem cell research & therapy* 1 28.

Gallego M J, Porayette P, Kaltcheva M M, Meethal S V & Atwood C S 2009 Opioid and progesterone signaling is obligatory for early human embryogenesis. *Stem cells and development* 18 737-740.

Gameiro C & Romao F 2010 Changes in the immune system during menopause and aging. *Frontiers in bioscience* 2 1299-1303.

Gameiro C M, Romao F & Castelo-Branco C 2010 Menopause and aging: changes in the immune system—a review. *Maturitas* 67 316-320.

Gapstur S M, Gann P H, Kopp P, Colangelo L, Longcope C & Liu K 2002 Serum androgen concentrations in young men: a longitudinal analysis of associations with age, obesity, and race. The CARDIA male hormone study. *Cancer epidemiology, biomarkers & prevention: a publication of the American Association for Cancer Research, cosponsored by the American Society of Preventive Oncology* 11 1041-1047.

Gharib S D, Wierman M E, Shupnik M A & Chin W W 1990 Molecular biology of the pituitary gonadotropins. *Endocrine reviews* 11 177-199.

Gleason C E, Cholerton B, Carlsson C M, Johnson S C & Asthana S 2005 Neuroprotective effects of female sex steroids in humans: current controversies and future directions. *Cellular and molecular life sciences: CMLS* 62 299-312.

Gray P C, Bilizikjian L M & Vale W 2002 Antagonism of activin by inhibin and inhibin receptors: a functional role for betaglycan. *Mol. Cell. Endocrinol.* 188 254-260.

Hahn W C & Meyerson M 2001 Telomerase activation, cellular immortalization and cancer. *Annals of medicine* 33 123-129.

Harman S M, Metter E J, Tobin J D, Pearson J & Blackman M R 2001 Longitudinal effects of aging on serum total and free testosterone levels in healthy men. Baltimore Longitudinal Study of Aging. *The Journal of clinical endocrinology and metabolism* 86 724-731.

Hayes F J, DeCruz S, Seminara S B, Boepple P A & Crowley W F, Jr. 2001a Differential regulation of gonadotropin secretion by testosterone in the human male: absence of a negative feedback effect of testosterone on follicle-stimulating hormone secretion. *The Journal of clinical endocrinology and metabolism* 86 53-58.

Hayes F J, Hall J E, Boepple P A & Crowley W F, Jr. 1998 Clinical review 96: Differential control of gonadotropin secretion in the human: endocrine role of inhibin. *The Journal of clinical endocrinology and metabolism* 83 1835-1841.

Hayes F J, Pitteloud N, DeCruz S, Crowley W F, Jr. & Boepple P A 2001b Importance of inhibin B in the regulation of FSH secretion in the human male. *The Journal of clinical endocrinology and metabolism* 86 5541-5546.

Hayward C J, Fradette J, Galbraith T, Remy M, Guignard R, Gauvin R, Germain L & Auger F A 2013 Harvesting the potential of the human umbilical cord: isolation and characterisation of four cell types for tissue engineering applications. *Cells, tissues, organs* 197 37-54.

Hockemeyer D, Soldner F, Cook E G, Gao Q, Mitalipova M & Jaenisch R 2008 A drug-inducible system for direct reprogramming of human somatic cells to pluripotency. *Cell stem cell* 3 346-353.

Illingworth P J, Groome N P, Byrd W, Rainey W E, McNeilly A S, Mather J P & Bremner W J 1996 Inhibin-B: a likely candidate for the physiologically important form of inhibin in men. *The Journal of clinical endocrinology and metabolism* 81 1321-1325.

Jacobsen M 1991 Histogenesis and morphogenesis of cortical structures. In *Developmental neurobiology*, pp 401-451. Ed M Jacobsen. New York: Plenum.

Jaffe R B & Keye W R, Jr. 1974 Estradiol augmentation of pituitary responsiveness to gonadotropin-releasing hormone in women. *The Journal of clinical endocrinology and metabolism* 39 850-855.

Jaffe R B & Keye W R, Jr. 1975 Modulation of pituitary response to hypothalamic releasing factors. *Journal of steroid biochemistry* 6 1055-1060.

Jaffe R B, Keye W R, Jr. & Young J R 1976 The role of estradiol in modulating LH and FSH response to gonadotropin releasing hormone. *Current topics in molecular endocrinology* 3 211-254.

Keye W R, Jr. & Jaffe R B 1974 Modulation of pituitary gonadotropin response to gonadotropin-releasing hormone by estradiol. *The Journal of clinical endocrinology and metabolism* 38 805-810.

Keye W R, Jr. & Jaffe R B 1975 Strength-duration characteristics of estrogen effects on gonadotropin response to gonadotropin-releasing hormone in women. I. Effects of varying duration of estradiol administration. *The Journal of clinical endocrinology and metabolism* 41 1003-1008.

Keye W R, Jr. & Jaffe R B 1976 Changing patterns of FSH and LH response to gonadotropin-releasing hormone in the puerperium. *The Journal of clinical endocrinology and metabolism* 42 1133-1138.

Knight P G & Glister C 2001 Potential local regulatory functions of inhibins, activins and follistatin in the ovary. *Reproduction* 121 503-512.

Kuhbier J W, Weyand B, Radtke C, Vogt P M, Kasper C & Reimers K 2010 Isolation, characterization, differentiation, and application of adipose-derived stem cells. *Advances in biochemical engineering/biotechnology* 123 55-105.

Lambert-Messerlian G M, Hall J E, Sluss P M, Taylor A E, Martin K A, Groome N P, Crowley W F, Jr. & Schneyer A L 1994 Relatively low levels of dimeric inhibin circulate in men and women with polycystic ovarian syndrome using a specific two-site enzyme-linked immunosorbent assay. *The Journal of clinical endocrinology and metabolism* 79 45-50.

le Nestour E, Marraoui J, Lahlou N, Roger M, de Ziegler D & Bouchard P 1993 Role of estradiol in the rise in follicle-stimulating hormone levels during the luteal-follicular transition. *The Journal of clinical endocrinology and metabolism* 77 439-442.

Lincoln G A 2001 The irritable male syndrome. *Reproduction, fertility, and development* 13 567-576.

Ling N, Ying S Y, Ueno N, Shimasaki S, Esch F, Hotta M & Guillemin R 1986 Pituitary FSH is released by a heterodimer of the beta-subunits from the two forms of inhibin. *Nature* 321 779-782.

Liu J H & Yen S S 1983 Induction of midcycle gonadotropin surge by ovarian steroids in women: a critical evaluation. *The Journal of clinical endocrinology and metabolism* 57 797-802.

Liu P Y, Beilin J, Meier C, Nguyen T V, Center J R, Leedman P J, Seibel M J, Eisman J A & Handelsman D J 2007 Age-related changes in serum testosterone and sex hormone binding globulin in Australian men: longitudinal analyses of two geographically separate regional cohorts. *The Journal of clinical endocrinology and metabolism* 92 3599-3603.

Llaneza P, Fernandez-Inarrea J M, Arnott B, Garcia-Portilla M P, Chedraui P & Perez-Lopez F R 2011 Sexual function assessment in postmenopausal women with the 14-item changes in sexual functioning questionnaire. *The journal of sexual medicine* 8 2144-2151.

Llaneza P, Garcia-Portilla M P, Llaneza-Suarez D, Armott B & Perez-Lopez F R 2012 Depressive disorders and the menopause transition. *Maturitas* 71 120-130.

Lo K C, Lei Z, Rao Ch V, Beck J & Lamb D J 2004 De novo testosterone production in luteinizing hormone receptor knockout mice after transplantation of leydig stem cells. *Endocrinology* 145 4011-4015.

Ludwig T E, Bergendahl V, Levenstein M E, Yu J, Probasco M D & Thomson J A 2006 Feeder-independent culture of human embryonic stem cells. *Nature methods* 3 637-646.

Lusis A J 2000 Atherosclerosis. *Nature* 407 233-241.

Malgieri A, Kantzari E, Patrizi M P & Gambardella S 2010 Bone marrow and umbilical cord blood human mesenchymal stem cells: state of the art. *International journal of clinical and experimental medicine* 3 248-269.

Manini I, Gulino L, Gaya B, Pierantozzi E, Curina C, Rossi D, Brafa A, D'Aniello C & Sorrentino V 2011 Multipotent progenitors in freshly isolated and cultured human mesenchymal stem cells: a comparison between adipose and dermal tissue. *Cell and tissue research* 344 85-95.

Marynick S P, Loriaux D L, Sherins R J, Pita J C, Jr. & Lipsett M B 1979 Evidence that testosterone can suppress pituitary gonadotropin secretion independently of peripheral aromatization. *The Journal of clinical endocrinology and metabolism* 49 396-398.

Mason J B, Cargill S L, Anderson G B & Carey J R 2009 Transplantation of young ovaries to old mice increased life span in transplant recipients. *J Gerontol A Biol Sci Med Sci* 64 1207-1211.

McPhie D L, Coopersmith R, Hines-Peralta A, Chen Y, Ivins K J, Manly S P, Kozlowski M R, Neve K A & Neve R L 2003 DNA synthesis and neuronal apoptosis caused by familial Alzheimer disease mutants of the amyloid precursor protein are mediated by the p21 activated kinase PAK3. *The Journal of neuroscience: the official journal of the Society for Neuroscience* 23 6914-6927.

Meethal S V, Liu T, Chan H W, Ginsburg E, Wilson A C, Gray D N, Bowen R L, Vonderhaar B K & Atwood C S 2009 Identification of a regulatory loop for the synthesis of neurosteroids: a steroidogenic acute regulatory protein-dependent mechanism involving hypothalamic-pituitary-gonadal axis receptors. *J Neurochem* 110 1014-1027.

Meethal S V, Smith M A, Bowen R L & Atwood C S 2005 The gonadotropin connection in Alzheimer's disease. *Endocrine* 26 317-326.

Monterrosa-Castro A, Marrugo-Florez M, Romero-Perez I, Chedraui P, Fernandez-Alonso A M & Perez-Lopez F R 2013 Prevalence of insomnia and related factors in a large mid-aged female Colombian sample. *Maturitas* 74 346-351.

Monterrosa-Castro A, Romero-Perez I, Marrugo-Florez M, Fernandez-Alonso A M, Chedraui P & Perez-Lopez F R 2012 Quality of life in a large cohort of mid-aged Colombian women assessed using the Cervantes Scale. *Menopause* 19 924-930.

Multani A S, Ozen M, Narayan S, Kumar V, Chandra J, McConkey D J, Newman R A & Pathak S 2000 Caspase-dependent apoptosis induced by telomere cleavage and TRF2 loss. *Neoplasia* 2 339-345.

Ornat L, Martinez-Dearth R, Munoz A, Franco P, Alonso B, Tajada M & Perez-Lopez F R 2013 Sexual function, satisfaction with life and menopausal symptoms in middle-aged women. *Maturitas* 75 261-269.

Ossewaarde M E, Bots M L, Verbeek A L, Peeters P H, van der Graaf Y, Grobbee D E & van der Schouw Y T 2005 Age at menopause, cause-specific mortality and total life expectancy. *Epidemiology* 16 556-562.

Paganini-Hill A, Corrada M M & Kawas C H 2006 Increased longevity in older users of postmenopausal estrogen therapy: the Leisure World Cohort Study. *Menopause* 13 12-18.

Parker W H & Manson J E 2009 Oophorectomy and cardiovascular mortality: is there a link? *Menopause* 16 1-2.

Perez-Lopez F R, Fernandez-Alonso A M, Trabalon-Pastor M, Vara C & Chedraui P 2012 Assessment of sexual function and related factors in mid-aged sexually active Spanish women with the six-item Female Sex Function Index. *Menopause* 19 1224-1230.

Pien G W, Sammel M D, Freeman E W, Lin H & DeBlasis T L 2008 Predictors of sleep quality in women in the menopausal transition. *Sleep* 31 991-999.

Pitteloud N, Dwyer A A, DeCruz S, Lee H, Boepple P A, Crowley W F, Jr. & Hayes F J 2008a Inhibition of luteinizing hormone secretion by testosterone in men requires aromatization for its pituitary but not its hypothalamic effects: evidence from the tandem study of normal and gonadotropin-releasing hormone-deficient men. *The Journal of clinical endocrinology and metabolism* 93 784-791.

Pitteloud N, Dwyer A A, DeCruz S, Lee H, Boepple P A, Crowley W F, Jr. & Hayes F J 2008b The relative role of gonadal sex steroids and gonadotropin-releasing hormone pulse frequency in the regulation of follicle-stimulating hormone secretion in men. *The Journal of clinical endocrinology and metabolism* 93 2686-2692.

Porayette P, Gallego M J, Kaltcheva M M, Bowen R L, Vadakkadath Meethal S & Atwood C S 2009 Differential processing of amyloid-beta precursor protein directs human embryonic stem cell proliferation and differentiation into neuronal precursor cells. *The Journal of biological chemistry* 284 23806-23817.

Ratajczak M Z, Zuba-Surma E K, Wojakowski W, Ratajczak J & Kucia M 2008 Bone Marrow—Home of Versatile Stem Cells. *Transfusion medicine and hemotherapy: offizielles Organ der Deutschen Gesellschaft fur Transfusionsmedizin and Immunhamatologie* 35 248-259.

Reichlin S 1998 Williams Textbook of Endocrinology. In *Williams Textbook of Endocrinology*. 10 ed, pp 165-248. Eds J D Wilson, D W Foster, H M Kronenberg & P R Larsen. Philadelphia Pa.: WB Saunders Co.

Rocca W A, Grossardt B R, de Andrade M, Malkasian G D & Melton L J, 3rd 2006 Survival patterns after oophorectomy in premenopausal women: a population-based cohort study. *The lancet oncology* 7 821-828.

Rocca W A, Grossardt B R, Geda Y E, Gostout B S, Bower J H, Maraganore D M, de Andrade M & Melton L J, 3rd 2008 Long-term risk of depressive and anxiety symptoms after early bilateral oophorectomy. *Menopause* 15 1050-1059.

Rocca W A, Grossardt B R, Miller V M, Shuster L T & Brown R D, Jr. 2012 Premature menopause or early menopause and risk of ischemic stroke. *Menopause* 19 272-277.

Rosario E R, Chang L, Head E H, Stanczyk F Z & Pike C J 2011 Brain levels of sex steroid hormones in men and women during normal aging and in Alzheimer's disease. *Neurobiology of Aging* 32 604-613.

Rosario E R, Chang L, Stanczyk F Z & Pike C J 2004 Age-related testosterone depletion and the development of Alzheimer disease. *JAMA: the journal of the American Medical Association* 292 1431-1432.

Santen R J 1975 Is aromatization of testosterone to estradiol required for inhibition of luteinizing hormone secretion in men? *The Journal of clinical investigation* 56 1555-1563.

Schnorr J A, Bray M J & Veldhuis J D 2001 Aromatization mediates testosterone's short-term feedback restraint of 24-hour endogenously driven and acute exogenous gonadotropin-releasing hormone-stimulated luteinizing hormone and follicle-stimulating hormone secretion in young men. *The Journal of clinical endocrinology and metabolism* 86 2600-2606.

Sherins R J & Loriaux D L 1973 Studies of the role of sex steroids in the feedback control of FSH concentrations in men. *The Journal of clinical endocrinology and metabolism* 36 886-893.

Simon A F, Shih C, Mack A & Benzer S 2003 Steroid control of longevity in Drosophila melanogaster. *Science* 299 1407-1410.

Sittadjody S, Saul J M, Joo S, Yoo J J, Atala A & Opara E C 2013 Engineered multilayer ovarian tissue that secretes sex steroids and peptide hormones in response to gonadotropins. *Biomaterials* 34 2412-2420.

Steiner R A, Bremner W J & Clifton D K 1982 Regulation of luteinizing hormone pulse frequency and amplitude by testosterone in the adult male rat. *Endocrinology* 111 2055-2061.

Sternbach H 1998 Age-associated testosterone decline in men: clinical issues for psychiatry. *The American journal of psychiatry* 155 1310-1318.

Sun L, Peng Y, Sharrow A C, Iqbal J, Zhang Z, Papachristou D J, Zaidi S, Zhu L L, Yaroslayskiy B B, Zhou H, et al. 2006 FSH directly regulates bone mass. *Cell* 125 247-260.

T'Sjoen G G, De Vos S, Goemaere S, Van Pottelbergh I, Dierick M, Van Heeringen C & Kaufman J M 2005 Sex steroid level, androgen receptor polymorphism, and depressive symptoms in healthy elderly men. *Journal of the American Geriatrics Society* 53 636-642.

Taylor A E, Whitney H, Hall J E, Martin K & Crowley W F, Jr. 1995 Midcycle levels of sex steroids are sufficient to recreate the follicle-stimulating hormone but not the luteinizing hormone midcycle surge: evidence for the contribution of other ovarian factors to the surge in normal women. *The Journal of clinical endocrinology and metabolism* 80 1541-1547.

Tholpady S S, Katz A J & Ogle R C 2003 Mesenchymal stem cells from rat visceral fat exhibit multipotential differentiation in vitro. *The anatomical record. Part A, Discoveries in molecular, cellular, and evolutionary biology* 272 398-402.

Thorner M, Vance M, Laws Jr. E, Horvath E & Kovacs K 1998 Williams Textbook of Endocrinology. pp 249-340. Ed F D Wilson J D, Kronenberg H M, Larsen P R. Philadelphia Pa.: WB Saunders Co.

Travison T G, Araujo A B, Kupelian V, O'Donnell A B & McKinlay J B 2007a The relative contributions of aging, health, and lifestyle factors to serum testosterone decline in men. *The Journal of clinical endocrinology and metabolism* 92 549-555.

Travison T G, Araujo A B, O'Donnell A B, Kupelian V & McKinlay J B 2007b A population-level decline in serum testosterone levels in American men. *The Journal of clinical endocrinology and metabolism* 92 196-202.

Tserotas K & Merino G 1998 Andropause and the aging male. *Archives of andrology* 40 87-93.

Tuli R, Seghatoleslami M R, Tuli S, Wang M L, Hozack W J, Manner P A, Danielson K G & Tuan R S 2003a A simple, high-yield method for obtaining multipotential mesenchymal progenitor cells from trabecular bone. *Molecular biotechnology* 23 37-49.

Tuli R, Tuli S, Nandi S, Wang M L, Alexander P G, Haleem-Smith H, Hozack W J, Manner P A, Danielson K G & Tuan R S 2003b Characterization of multipotential mesenchymal progenitor cells derived from human trabecular bone. *Stem Cells* 21 681-693.

Vadakkadath Meethal S & Atwood C S 2005 The role of hypothalamic-pituitary-gonadal hormones in the normal structure and functioning of the brain. *Cell Mol Life Sci* 62 257-270.

Vadakkadath Meethal S, Gallego M J, Haasl R J, Petras S J, 3rd, Sgro J Y & Atwood C S 2006 Identification of a gonadotropin-releasing hormone receptor orthologue in *Caenorhabditis elegans*. *BMC evolutionary biology* 6 103.

Vale W, Rivier J, Vaughn J, McClintock R, Corrigan A, Woo W, Darr D & Spiess J 1986 Purification and characterization of an FSH releasing protein from porcine ovarian follicular fluid. *Nature* 321 776-779.

Veldhuis J D, Urban R J & Dufau M L 1992 Evidence that androgen negative feedback regulates hypothalamic gonadotropin-releasing hormone impulse strength and the burst-like secretion of biologically active luteinizing hormone in men. *The Journal of clinical endocrinology and metabolism* 74 1227-1235.

Wallace W H & Kelsey T W 2010 Human ovarian reserve from conception to the menopause. *PLoS One* 5 e8772.

Welt C K, Martin K A, Taylor A E, Lambert-Messerlian G M, Crowley W F, Jr., Smith J A, Schoenfeld D A & Hall J E 1997 Frequency modulation of follicle-stimulating hormone (FSH) during the luteal-follicular transition: evidence for FSH control of inhibin B in normal women. *The Journal of clinical endocrinology and metabolism* 82 2645-2652.

Wilson A C, Clemente L, Liu T, Bowen R L, Meethal S V & Atwood C S 2008 Reproductive hormones regulate the selective permeability of the blood-brain barrier. *Biochim Biophys Acta* 1782 401-407.

Wilson A C, Salamat M S, Haasl R J, Roche K M, Karande A, Meethal S V, Terasawa E, Bowen R L & Atwood C S 2006 Human neurons express type I GnRH receptor and respond to GnRH I by increasing luteinizing hormone expression. *The Journal of endocrinology* 191 651-663.

Winters S J, Janick J J, Loriaux D L & Sherins R J 1979a Studies on the role of sex steroids in the feedback control of gonadotropin concentrations in men. II. Use of the estrogen antagonist, clomiphene citrate. *The Journal of clinical endocrinology and metabolism* 48 222-227.

Winters S J, Sherins R J & Loriaux D L 1979b Studies on the role of sex steroids in the feedback control of gonadotropin concentrations in men. III. Androgen resistance in primary gonadal failure. *The Journal of clinical endocrinology and metabolism* 48 553-558.

Yazawa T, Mizutani T, Yamada K, Kawata H, Sekiguchi T, Yoshino M, Kajitani T, Shou Z, Umezawa A & Miyamoto K 2006 Differentiation of adult stem cells derived from bone marrow stroma into Leydig or adrenocortical cells. *Endocrinology* 147 4104-4111.

Ying S Y 1988 Inhibins, activins, and follistatins: gonadal proteins modulating the secretion of follicle-stimulating hormone. *Endocrine reviews* 9 267-293.

Yonker J A, Chang V, Roetker N S, Hauser T S, Hauser R M & Atwood C S 2011 Hypothalamic-pituitary-gonadal axis homeostasis predicts longevity. *AGE*.

Young J R & Jaffe R B 1976 Strength-duration characteristics of estrogen effects on gonadotropin response to gonadotropin-releasing hormone in women. II. Effects of varying concentrations of estradiol. *The Journal of clinical endocrinology and metabolism* 42 432-442.

Yu J, Hu K, Smuga-Otto K, Tian S, Stewart R, Slukvin, I I & Thomson J A 2009 Human induced pluripotent stem cells free of vector and transgene sequences. *Science* 324 797-801.

Yue X, Lu M, Lancaster T, Cao P, Honda S, Staufenbiel M, Harada N, Zhong Z, Shen Y & Li R 2005 Brain estrogen deficiency accelerates Abeta plaque formation in an Alzheimer's disease animal model. *Proc Natl Acad Sci USA* 102 19198-19203.

Zhu M, Heydarkhan-Hagvall S, Hedrick M, Benhaim P & Zuk P 2013 Manual isolation of adipose-derived stem cells from human lipoaspirates. *Journal of visualized experiments: JoVE* e50585.

Zuk P A, Zhu M, Mizuno H, Huang J, Futrell J W, Katz A J, Benhaim P, Lorenz H P & Hedrick M H 2001 Multilineage cells from human adipose tissue: implications for cell-based therapies. *Tissue engineering* 7 211-228.

What is claimed is:

1. A method of treating andropause in a subject in need thereof, the method comprising:
    measuring a pre-treatment concentration of circulating reproductive hormones in a hypothalamic-pituitary-gonadal (HPG) axis of the subject;
    administering to the subject a therapeutically effective amount of a plurality of types of donor cells wherein the andropause comprises dysregulation of the HPG axis of the subject, and wherein the plurality of types of donor cells act in concert to restore hormone ratios to those of a normal subject of 18 to 35 years of age, the donor cells including spermatogonia, Sertoli cells, myoid cells, Leydig cells, and macrophage cells; and
    measuring a post-treatment concentration of circulating reproductive hormones in the HPG axis of the subject to confirm the hormone ratios in the HPG axis of the subject to correspond to the normal subject of 18 to 35 years of age.

2. The method according to claim 1 wherein blood and/or tissue levels, production, function and activity of the subject, respectively, are regulated to the blood and/or tissue levels, production, function and activity corresponding to the normal subject at 18-35 years of age.

3. The method according to claim 1 wherein the ratios of hormones in the HPG axis of the subject are maintained at a ratio corresponding to the normal subject at 18-35 years of age.

4. The method according to claim 3 wherein the sex steroids, AMH kit ligand, inhibins and follistatin of the subject are regulated to be at the ratio corresponding to the normal at 18-35 years of age.

5. The method according to claim 3 wherein the kisspeptin, neurokinin B, dynorphin, GnRH, LH, FSH and activins are regulated to be at the ratio corresponding to the normal subject at 18-35 years of age.

6. The method according to claim 1 wherein the donor cells are administered parenterally for the treatment of at least one of: systemic conditions and diseases; tissue-specific conditions and diseases; for the regeneration of tissues; and for the restoration of function of tissues.

7. The method according to claim 1 wherein treatment increases longevity of the subject.

8. The method according to claim 1 further comprising the step of administering to the subject an additional therapeutically effective amount of the plurality of types of donor cells in response to the measured post-treatment concentration of circulating reproductive hormones in the HPG axis of the subject being dysregulated.

9. A method of treating andropause in a subject in need thereof, the method comprising:
    measuring a pre-treatment concentration of circulating reproductive hormones in a hypothalamic-pituitary-gonadal (HPG) axis of the subject;
    administering to the subject a therapeutically effective amount of a plurality of types of donor cells wherein the andropause comprises dysregulation of the HPG axis of the subject, and wherein the plurality of types of donor cells act in concert to restore hormone ratios to those of a normal subject of 18 to 35 years of age, the donor cells being Sertoli cells, ells, Leydig cells, and macrophage cells; and
    measuring a post-treatment concentration of circulating reproductive hormones in the HPG axis of the subject to confirm the hormone ratios in the HPG axis of the subject to correspond to the normal subject of 18 to 35 years of age.

10. The method according to claim 9 further comprising the step of administering to the subject an additional therapeutically effective amount of the plurality of types of donor cells in response to the measured post-treatment concentration of circulating reproductive hormones in the HPG axis of the subject being dysregulated.

11. A method of treating andropause in a subject in need thereof, the method comprising:
    measuring a pre-treatment concentration of circulating reproductive hormones in a hypothalamic-pituitary-gonadal (HPG) axis of the subject;
    administering to the subject a therapeutically effective amount of donor cells, the donor cells mesenchymal stem cells being in vitro differentiated into a plurality of differentiated cell types including each of Sertoli cells and Leydig cells, wherein the andropause comprises dysregulation of the HPG axis of the subject, and wherein the plurality of differentiated cell types act in concert to restore hormone ratios to those of a normal subject of 18 to 35 years of age; and
    measuring a post-treatment concentration of circulating reproductive hormones in the HPG axis of the subject to confirm the hormone ratios in the HPG axis of the subject to correspond to the normal subject of 18 to 35 years of age.

12. The method according to claim 11 wherein blood and/or tissue levels, production, function and activity of the subject, respectively, are regulated to the blood and/or tissue levels, production, function and activity corresponding to the normal subject at 18-35 years of age.

13. The method according to claim 11 wherein the ratios of hormones in the HPG axis of the subject are maintained at a ratio corresponding to the normal subject at 18-35 years of age.

14. The method according to claim 12 wherein the sex steroids, AMH kit ligand, inhibins and follistatin of the subject are regulated to be at the ratio corresponding to the normal at 18-35 years of age.

15. The method according to claim 12 wherein the kisspeptin, neurokinin B, dynorphin, GnRH, LH, FSH and activins are regulated to be at the ratio corresponding to the normal subject at 18-35 years of age.

16. The method according to claim 11 wherein the donor cells are administered parenterally for the treatment of at least one of: systemic conditions and diseases; tissue-specific conditions and diseases; for the regeneration of tissues; and for the restoration of function of tissues.

17. The method according to claim 11 wherein treatment increases longevity of the subject.

18. The method according to claim 11 further comprising the step of administering to the subject an additional therapeutically effective amount of the plurality of types of donor cells in response to the measured post-treatment concentration of circulating reproductive hormones in the HPG axis of the subject being dysregulated.

19. The method according to claim 11 wherein the plurality of differentiated cell types further include each of spermatogonia, myoid cells, and macrophage cells.

20. The method according to claim 9 wherein the plurality of differentiated cell types further include each of spermatogonia and myoid cells.

* * * * *

UNITED STATES PATENT AND TRADEMARK OFFICE
CERTIFICATE OF CORRECTION

| | |
|---|---|
| PATENT NO. | : 11,253,549 B2 |
| APPLICATION NO. | : 14/718390 |
| DATED | : February 22, 2022 |
| INVENTOR(S) | : Craig S. Atwood |

It is certified that error appears in the above-identified patent and that said Letters Patent is hereby corrected as shown below:

In the Claims

Claim 9, Line 37: "being" should be replaced with --including each of--

Claim 9, Line 37: please delete "ells,"

Claim 11, Line 3: the word "in vitro" should be italicized

Signed and Sealed this
Thirtieth Day of May, 2023

Katherine Kelly Vidal
*Director of the United States Patent and Trademark Office*